(12) United States Patent
Nitta et al.

(10) Patent No.: US 11,959,632 B2
(45) Date of Patent: Apr. 16, 2024

(54) LIGHT-EMITTING DEVICE, ELECTRONIC DEVICE, AND METHOD FOR USING LIGHT-EMITTING DEVICE

(71) Applicant: Panasonic Intellectual Property Management Co., Ltd., Osaka (JP)

(72) Inventors: Mitsuru Nitta, Kyoto (JP); Shozo Oshio, Osaka (JP); Takeshi Abe, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 282 days.

(21) Appl. No.: 17/418,278

(22) PCT Filed: Dec. 18, 2019

(86) PCT No.: PCT/JP2019/049558
§ 371 (c)(1),
(2) Date: Jun. 25, 2021

(87) PCT Pub. No.: WO2020/137731
PCT Pub. Date: Jul. 2, 2020

(65) Prior Publication Data
US 2022/0090759 A1 Mar. 24, 2022

(30) Foreign Application Priority Data

Dec. 27, 2018 (JP) ................ 2018-245494

(51) Int. Cl.
*F21V 9/30* (2018.01)
*A61B 5/00* (2006.01)
(Continued)

(52) U.S. Cl.
CPC .............. *F21V 9/30* (2018.02); *A61B 5/0071* (2013.01); *A61N 5/062* (2013.01); *A61N 5/067* (2021.08);
(Continued)

(58) Field of Classification Search
CPC . F21V 9/30; F21V 9/38; A61B 5/0071; A61N 5/062; F21W 2131/20
See application file for complete search history.

(56) References Cited

U.S. PATENT DOCUMENTS

| 5,202,777 A | 4/1993 | Sluzky |
| 5,512,210 A | 4/1996 | Sluzky |

(Continued)

FOREIGN PATENT DOCUMENTS

| CN | 107001931 A | 8/2017 |
| CN | 108467733 A | 8/2018 |

(Continued)

OTHER PUBLICATIONS

Extended European Search Report for corresponding EP Application No. 19902964.6 dated Jan. 25, 2022.

(Continued)

*Primary Examiner* — Sean P Gramling
(74) *Attorney, Agent, or Firm* — Renner, Otto, Boisselle & Sklar, LLP

(57) ABSTRACT

A light-emitting device includes: a light source that radiates primary light; and a first phosphor that absorbs the primary light and converts the primary light into first wavelength-converted light having a longer wavelength than the primary light, wherein the primary light is laser light, the first wavelength-converted light includes fluorescence based on electron energy transition of $Cr^{3+}$, and a fluorescence spectrum of the first wavelength-converted light has a maximum fluorescence intensity value in region of a wavelength exceeding 710 nm.

17 Claims, 7 Drawing Sheets

(51) Int. Cl.
*A61N 5/06* (2006.01)
*A61N 5/067* (2006.01)
*A61B 1/04* (2006.01)
*A61B 1/06* (2006.01)
*F21W 131/20* (2006.01)
*F21Y 115/30* (2016.01)

(52) U.S. Cl.
CPC ............ *A61B 1/043* (2013.01); *A61B 1/0653* (2013.01); *F21W 2131/20* (2013.01); *F21Y 2115/30* (2016.08)

(56) References Cited

U.S. PATENT DOCUMENTS

| | | |
|---|---|---|
| 10,214,429 B2 | 2/2019 | Nitta |
| 10,784,416 B2 | 9/2020 | Onuma |
| 2014/0284638 A1 | 9/2014 | Tanaka |
| 2015/0357532 A1 | 12/2015 | Onuma et al. |
| 2016/0372631 A1 | 12/2016 | Hasegawa et al. |
| 2017/0343188 A1 | 11/2017 | Oshio et al. |
| 2020/0048549 A1* | 2/2020 | Hong ................ C09K 11/7787 |
| 2020/0220053 A1 | 7/2020 | Schmidt et al. |

FOREIGN PATENT DOCUMENTS

| | | |
|---|---|---|
| CN | 108795424 A | 11/2018 |
| CN | 109964324 A | 7/2019 |
| JP | 5-156246 A | 6/1993 |
| JP | 2014-187196 A | 10/2014 |
| JP | 5812461 B | 11/2015 |
| JP | 2016-121226 A | 7/2016 |
| JP | 6206696 | 9/2017 |
| JP | 2018-41856 A | 3/2018 |
| WO | 2010/053341 A1 | 5/2010 |
| WO | 2014103671 A1 | 7/2014 |
| WO | 2015/146069 A1 | 10/2015 |
| WO | 2016/092743 A1 | 9/2017 |
| WO | 2017/164214 A1 | 9/2017 |
| WO | 2018/207703 A1 | 11/2018 |
| WO | 2019/063309 A1 | 4/2019 |

OTHER PUBLICATIONS

Search Report for corresponding CN Application No. 201980086220.1 dated Oct. 25, 2022, with English language machine translation.
International Search Report for corresponding Application No. PCT/JP2019/049558, dated Mar. 10, 2020.
Written Opinion for corresponding Application No. PCT/JP2019/049558, dated Mar. 10, 2020.

* cited by examiner

LIGHT-EMITTING DEVICE, ELECTRONIC DEVICE, AND METHOD FOR USING LIGHT-EMITTING DEVICE

TECHNICAL FIELD

The present disclosure relates to a light-emitting device, an electronic device, and a method for using the light-emitting device.

BACKGROUND ART

Heretofore, there has been known a light-emitting device using a $Cr^{3+}$-activated phosphor (configuration (P)). Moreover, there has been known a light-emitting device including: an LED chip that radiates incoherent light; and a near-infrared phosphor (configuration (Q)). Furthermore, there has been known a light-emitting device including: a light source that radiates coherent laser light, such as a laser diode; and a phosphor that radiates a red fluorescent component (hereinafter, this phosphor will be referred to as "red phosphor") (configuration (R)).

For example, PTL 1 discloses a light-emitting device that meets the configurations (P) and (Q), a light-emitting device using a YAG-based phosphor coactivated by $Cr^{3+}$ and $Ce^{3+}$. As the above-described YAG-based phosphor, there is used $Y_3Al_5O_{12}:Cr^{3+},Ce^{3+}$, $Lu_3Al_5O_{12}:Cr^{3+},Ce^{3+}$, $Y_3(Al,Ga)_5O_{12}:Cr^{3+},Ce^{3+}$, $(Y,Gd)_3Al_5O_{12}:Cr^{3+},Ce^{3+}$ or the like.

Moreover, PTL 2 discloses, as the light-emitting device that meets the configurations (P) and (Q), a plant growing illumination light source using a phosphor having a fluorescence peak in a wavelength region of 700 to 760 nm, which corresponds to a light absorption spectrum of a chromoprotein (phytochrome) owned by a plant. Specifically, PTL 2 discloses a plant growing illumination light source in which a $Gd_3Ga_5O_{12}:Cr^{3+}$ phosphor having a fluorescence peak in the wavelength region of 700 to 760 nm and blue LEDs are packaged. In accordance with this illumination light source, the wavelength region of 700 to 760 nm where the fluorescence peak of the phosphor is present corresponds to the light absorption spectrum of the chromoprotein (phytochrome), and accordingly, growth and differentiation of the plant can be controlled. Moreover, PTL 6 discloses an infrared light-emitting device that emits light in a wide band in a wavelength range where photosensitivity of a Si photodiode detector is high.

Furthermore, PTL 3 discloses, as a light-emitting device that meets the configuration (Q), a medical inspection device that outputs a reflection image or transmission image of a near-infrared light component applied to a biological tissue. This medical inspection device uses, as the near-infrared light component, a fluorescent component radiated by a phosphor including Nd and Yb which are rare earths as activators.

Moreover, PTL 4 discloses, as a light-emitting device that meets the configuration (R), an illuminating device applied with a variety of lasers, the illuminating device including: a laser diode; and a red phosphor activated by $Ce^{3+}$.

Note that the light-emitting devices which are described in PTLs 1 to 3 and 6 and do not meet the configuration (R) are those for simply obtaining output light containing the near-infrared light component suitable for growing a plant, and so on in order to provide such a plant growing illuminating device, and so on. That is, the light-emitting devices described in PTLs 1 to 3 and 6 do not solve the problem that the light output of the phosphor is saturated, the problem being intrinsic to light-emitting devices using laser light.

Hence, the light-emitting devices described in PTLs 1 to 3 and 6 do not extremely limit a shape and the like of the fluorescence spectrum radiated by the $Cr^{3+}$-activated phosphor in order to solve the problem that the light output of the phosphor is saturated, either.

Furthermore, as a first light-emitting device using the near-infrared phosphor, there mainly has been known a plant growing illuminating device. However, this first light-emitting device is the one for simply obtaining the output light containing the near-infrared light component suitable for growing a plant, and does not solve the problem that such a light output of the phosphor when the phosphor is subjected to high-density photoexcitation is saturated.

Moreover, as a second light-emitting device using the near-infrared phosphor, there has been known an illuminating device for an optical coherence tomography (OCT) device that outputs a reflection image and transmission image of the near-infrared light component applied to a biological tissue. However, this second light-emitting device relates to a medical illuminating device, and does not solve a problem of a decrease of energy conversion efficiency, which is caused by variations of an absorption wavelength of a drug, the problem being intrinsic to the medical technology using a fluorescence imaging method and a photodynamic therapy.

Moreover, as a light-emitting device using laser light, there has been known a light-emitting device that obtains output light of visible light by mainly using a phosphor activated by rare earth ions ($Ce^{3+}$ and $Eu^{2+}$). However, this light-emitting device is not the one for obtaining high output light of near-infrared light, which is based on electron energy transition of $Cr^{3+}$.

Note that, heretofore, such a light-emitting device that excites a phosphor by laser light has had a problem that the fluorescence output of the phosphor is saturated. Heretofore, in order to suppress the saturation of the fluorescence output, for example, as described in PTL 4 or 5, it has been conceived to be essential to use a phosphor, such as $Ce^{3+}$ and $Eu^{2+}$, which exhibits fluorescence based on parity-allowed transition and has a short afterglow (10 us or less). In particular, it has been conceived to be preferable to use a $Ce^{3+}$-activated phosphor that exhibits an ultrashort afterglow (10 to 100 ns).

CITATION LIST

Patent Literature

PTL 1: Japanese Unexamined Patent Application Publication No. 2016-121226
PTL 2: International Publication No. WO 2010/053341
PTL 3: Japanese Patent No. 5812461
PTL 4: Japanese Patent No. 6206696
PTL 5: International Publication No. WO 2016/092743
PTL 6: International Publication No. WO 2018/207703

SUMMARY OF INVENTION

However, there is a problem as below when the near-infrared light component, which is demanded in medical care and sensing, is attempted to be obtained by using a $Ce^{3+}$-activated phosphor and an $Eu^{2+}$-activated phosphor in the light-emitting device that excites the phosphor by the laser light. That is, it has been difficult to develop the phosphor since temperature quenching increases in addition to that a range of choice for materials for use in the phosphor is narrow, and accordingly, there has been a problem that the light-emitting device that radiates the near-infrared light component cannot be obtained.

The present disclosure has been made in order to solve such a problem. The present disclosure has been achieved by finding that, when a phosphor containing, as an activator, $Cr^{3+}$ that radiates fluorescence with a long afterglow (10 μs or more) based on parity-forbidden transition is used, the saturation of the fluorescence output is less likely to occur even under high-density laser light excitation against the conventional technical common sense.

The above-described finding is largely different from the conventional technical common sense that it is essential to use a phosphor with a short afterglow (less than 10 μs) in order to suppress the saturation of the fluorescence output, and is surprising.

It is an object of the present disclosure to provide a light-emitting device that radiates high-output light with a high ratio of a near-infrared fluorescent component under excitation of high-density laser light, to provide an electronic device using the light-emitting device, and to provide a method for using the light-emitting device.

In order to solve the above-described problem, a light-emitting device according to a first aspect of the present disclosure is a light-emitting device including: a light source that radiates primary light; and a first phosphor that absorbs the primary light and converts the primary light into first wavelength-converted light having a longer wavelength than the primary light, wherein the primary light is laser light, the first wavelength-converted light includes fluorescence based on electron energy transition of $Cr^{3+}$, and a fluorescence spectrum of the first wavelength-converted light has a maximum fluorescence intensity value in region of a wavelength exceeding 710 nm.

A light-emitting device according to a second aspect of the present disclosure is a light-emitting device including: a light source that radiates primary light; and a first phosphor that absorbs the primary light and converts the primary light into first wavelength-converted light having a longer wavelength than the primary light, wherein the primary light is laser light, the first wavelength-converted light includes fluorescence based on electron energy transition of $Cr^{3+}$, and an 80% spectrum width in a maximum fluorescence intensity value peak of the first wavelength-converted light is 20 nm or more and less than 80 nm.

A light-emitting device according to a third aspect of the present disclosure is a light-emitting device including: a light source that radiates primary light; and a first phosphor that absorbs the primary light and converts the primary light into first wavelength-converted light having a longer wavelength than the primary light, wherein the primary light is laser light, the first wavelength-converted light includes fluorescence based on electron energy transition of $Cr^{3+}$, and a ratio of a fluorescence intensity of a fluorescence spectrum of the first wavelength-converted light at a wavelength of 780 nm with respect to a maximum fluorescence intensity value of the first wavelength-converted light exceeds 30%.

A light-emitting device according to a fourth aspect of the present disclosure is a light-emitting device including: a light source that radiates primary light; and a first phosphor that absorbs the primary light and converts the primary light into first wavelength-converted light having a longer wavelength than the primary light, wherein the primary light is laser light, the first wavelength-converted light includes fluorescence based on electron energy transition of $Cr^{3+}$, and a 1/10 afterglow of the first wavelength-converted light is less than 1 ms.

An electronic device according to a fifth aspect of the present disclosure includes: the light-emitting device according to any one of the first to fourth aspects of the present disclosure.

A method for using a light-emitting device according to a sixth aspect of the present disclosure is a method for using the light-emitting device according to any one of the first to fourth aspects of the present disclosure, wherein the light-emitting device is an illuminating device for a medical system using a fluorescence imaging method or a photodynamic therapy, and the method includes: a step of administering a fluorescent drug or a photosensitive drug to a subject; and applying the first wavelength-converted light to the subject with whom the fluorescent drug or the photosensitive drug is in contact.

DESCRIPTION OF EMBODIMENTS

Figure 1:
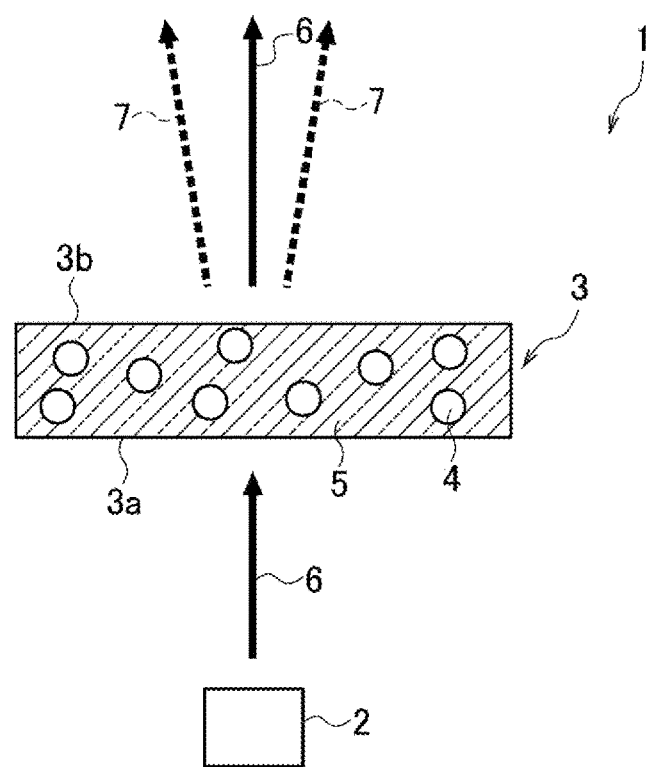
FIG. 1 is a schematic cross-sectional view illustrating an example of a light-emitting device according to a first embodiment.

A description will be given below of a light-emitting device according to this embodiment with reference to the drawings. Note that dimensional ratios in the drawings are exaggerated for convenience of explanation, and are sometimes different from actual ratios.

[Light-Emitting Device]

Figure 2:
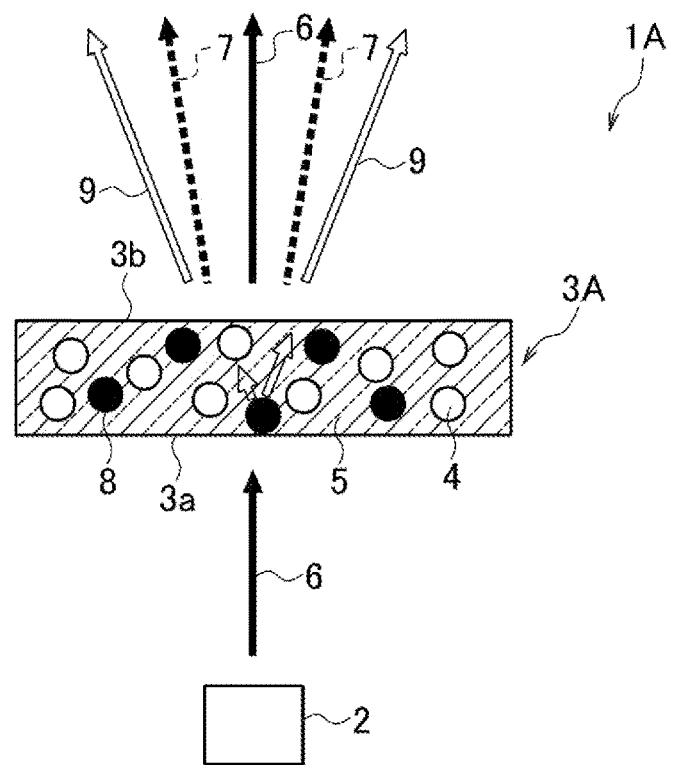
FIG. 2 is a schematic cross-sectional view illustrating an example of a light-emitting device according to a second embodiment.
Figure 3:
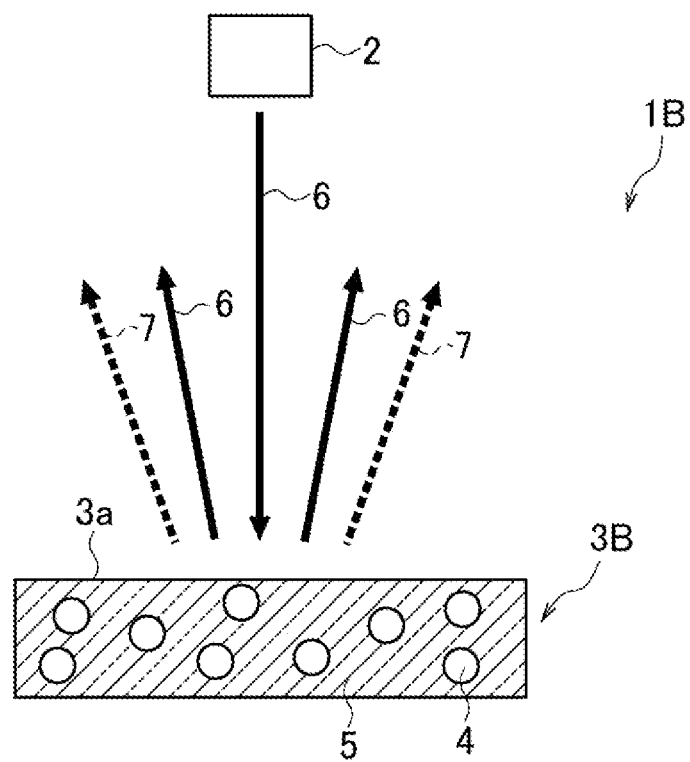
FIG. 3 is a schematic cross-sectional view illustrating an example of a light-emitting device according to a third embodiment.
Figure 4:
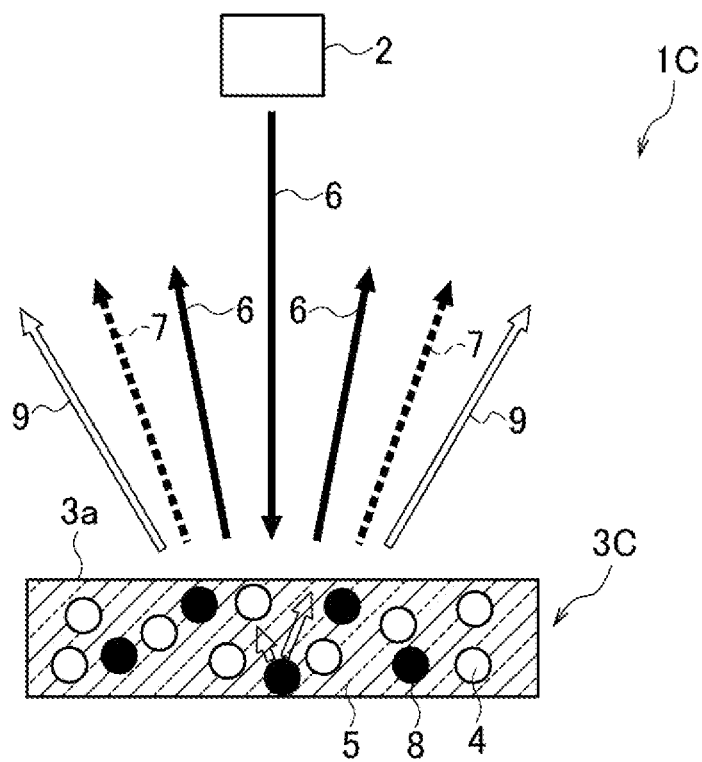
FIG. 4 is a schematic cross-sectional view illustrating an example of a light-emitting device according to a fourth embodiment.

FIGS. 1 to 4 illustrate light-emitting devices 1, 1A, 1B and 1C according to this embodiment. FIG. 1 is a schematic cross-sectional view illustrating an example of a light-emitting device according to a first embodiment. FIG. 2 is a schematic cross-sectional view illustrating an example of a light-emitting device according to a second embodiment. FIG. 3 is a schematic cross-sectional view illustrating an example of a light-emitting device according to a third embodiment. FIG. 4 is a schematic cross-sectional view illustrating an example of a light-emitting device according to a fourth embodiment.

Each of the light-emitting devices 1, 1A, 1B and 1C according to this embodiment is an example of a medical light-emitting device. As illustrated in FIGS. 1 to 4, each of the light-emitting devices 1, 1A, 1B and 1C includes a light source 2 and a first phosphor 4 in common.

Note that, in each of the light-emitting devices 1 and 1B, the first phosphor 4 is included in a wavelength converter 3, and in each of the light-emitting devices 1A and 1C, the first phosphor 4 is included in a wavelength converter 3A. Therefore, each of the light-emitting devices 1 and 1B includes the light source 2, and the wavelength converter 3 including the first phosphor 4. Moreover, each of the light-emitting devices 1A and 1C includes the light source 2, and the wavelength converter 3A including the first phosphor 4.

Each of the light-emitting devices 1, 1A, 1B and 1C is configured so that a phosphor such as the first phosphor 4 included in the wavelength converter 3 or 3A radiates fluorescence when primary light 6 radiated from the light source 2 enters the wavelength converter 3 or 3A. Moreover, the first phosphor 4 is configured to, upon receiving the primary light 6, radiate first wavelength-converted light including fluorescence based on electron energy transition of $Cr^{3+}$ and having a maximum fluorescence intensity value in a region of a wavelength exceeding 710 nm.

Note that each of the wavelength converter 3 of the light-emitting device 1 illustrated in FIG. 1 and the wavelength converter 3A of the light-emitting device 1A illustrated in FIG. 2 has a configuration to receive the primary light 6 by a front surface 3a and to radiate fluorescence from a back surface 3b. Moreover, each of the wavelength converter 3 of the light-emitting device 1B illustrated in FIG. 3 and the wavelength converter 3A of the light-emitting device 1C illustrated in FIG. 4 has a configuration to receive the primary light 6 by the front surface 3a and to radiate fluorescence from the same front surface 3a.

Each of the light-emitting devices 1, 1A, 1B and 1C radiates the first wavelength-converted light in which a broad spectral component having a maximum fluorescence intensity value in such a wavelength region exceeding 710 nm is larger in amount than a linear spectral component having a maximum fluorescence intensity value in a wavelength region of 680 to 710 nm. Therefore, each of the light-emitting devices 1, 1A, 1B and 1C is a light-emitting device of a point light source including a large amount of a near-infrared component.

Note that the above-described linear spectral component is a light component with a long afterglow, which is based on electron energy transition (spin-forbidden transition) of $^2T_1$ and $^2E \rightarrow {}^4A_2$ in $Cr^{3+}$. Moreover, the above-described broad spectral component is a light component with a short afterglow, which is based on electron energy transition (spin-allowed transition) of $^4T_2 \rightarrow {}^4A_2$. Such a mechanism of the fluorescence by $Cr^{3+}$ will be described later. The light-emitting devices 1, 1A, 1B and 1C will be described below.

First Embodiment

The light-emitting device 1 according to the first embodiment will be described.

(Light Source)

The light source 2 radiates the primary light 6. Laser light is used as the primary light 6. As the laser light, for example, used is laser light including at least either one of cold color light having a maximum fluorescence intensity value within a wavelength range of 400 nm or more and less than 500 nm and warm color light having a maximum fluorescence intensity value within a wavelength range of 570 nm or more and less than 660 nm. As the cold color light, preferably, light having a maximum fluorescence intensity value within a wavelength range of 430 nm or more and less than 480 nm is used. As the warm color light, preferably, light having a maximum fluorescence intensity value within a wavelength range of 590 nm or more and less than 640 nm is used.

When the laser light including at least either one of the above-described cold color light and the above-described warm color light is used as the primary light 6, the laser light is well absorbed to the first phosphor 4 activated by $Cr^{3+}$, and is efficiently subjected to wavelength conversion into first wavelength-converted light 7. Therefore, in accordance with the light-emitting device 1 in which the laser light including at least either one of the above-described cold color light and the above-described warm color light is used as the primary light 6, it is possible to radiate output light with a high ratio of a fluorescent component based on electron energy transition of $Cr^{3+}$.

As the light source 2, there is used a cold color light laser element that radiates laser light of a color of the above-described cold color light or a warm color light laser element that radiates laser light of a color of the above-described warm color light. As the cold color light laser element, a blue laser element that radiates blue laser light is preferably used. As the warm color light laser element, a red laser element that radiates red laser light is preferably used. When the light source 2 is the cold color light laser element or the warm color light laser element, the phosphor in each of the wavelength converters 3 and 3A is excited highly efficiently, and accordingly, each of the light-emitting devices 1, 1A, 1B and 1C becomes capable of radiating high-output near-infrared light.

Note that, with regard to the blue laser element in the cold color light laser element, a high-efficiency and high-output laser element is easily available. Therefore, it is preferable to use the blue laser element as the light source 2 in terms of achieving an increase of the output of the light-emitting device. Moreover, in the red laser element in the warm color light laser element, an energy difference thereof from a near-infrared light component is small, and an energy loss following the wavelength conversion is small. Therefore, it is preferable to use the red laser element as the light source 2 in terms of achieving an increase of the efficiency of the light-emitting device.

For example, a surface-emitting laser diode is used as the light source 2. Moreover, the light source 2 is a solid-state light-emitting element in which a rated light output is usually 1 W or more, preferably 3 W or more. When the rated light output of the light source 2 is within the above-described range, the high-output primary light 6 is radiated, and therefore, it is possible to increase the output of the light-emitting device 1.

Note that an upper limit of the rated light output is not particularly limited. The light source 2 is composed of a plurality of solid-state light-emitting elements, thus making it possible to increase the output of the light source 2. However, considering practicality, the rated light output of the light source 2 is usually less than 10 kW, preferably less than 3 kW.

A light density of the primary light 6 applied to the first phosphor 4 is set to usually exceed 0.5 $W/mm^2$, preferably exceed 3 $W/mm^2$, more preferably exceed 10 $W/mm^2$, still more preferably exceed 30 $W/mm^2$. When the light density of the primary light 6 is within the above-described range, the first phosphor 4 is excited by high-density light, thus making it possible for the light-emitting device 1 to radiate a high-output fluorescent component. Note that, when a high-output LED with an output exceeding 0.5 $W/mm^2$ is developed by a power increase of LEDs in the future, the high-output LED can also be used like the above-described laser.

(Wavelength Converter)

The wavelength converter 3 includes the first phosphor 4 and a sealing material 5. In the wavelength converter 3, the first phosphor 4 is included in the sealing material 5.

<First Phosphor>

The first phosphor 4 is a phosphor that absorbs the primary light 6 and converts the primary light 6 into the first wavelength-converted light 7 with a longer wavelength than that of the primary light 6. The first phosphor 4 absorbs the primary light 6, and radiates the first wavelength-converted light 7 including the fluorescence based on the electron energy transition of $Cr^{3+}$. That is, the first wavelength-converted light 7 includes the fluorescence based on the electron energy transition of $Cr^{3+}$. Here, the fluorescence based on the electron energy transition of $Cr^{3+}$ means fluorescence based on the electron energy transition (spin-allowed transition) of $^4T_2 \to {}^4A_2$.

Figure 5:
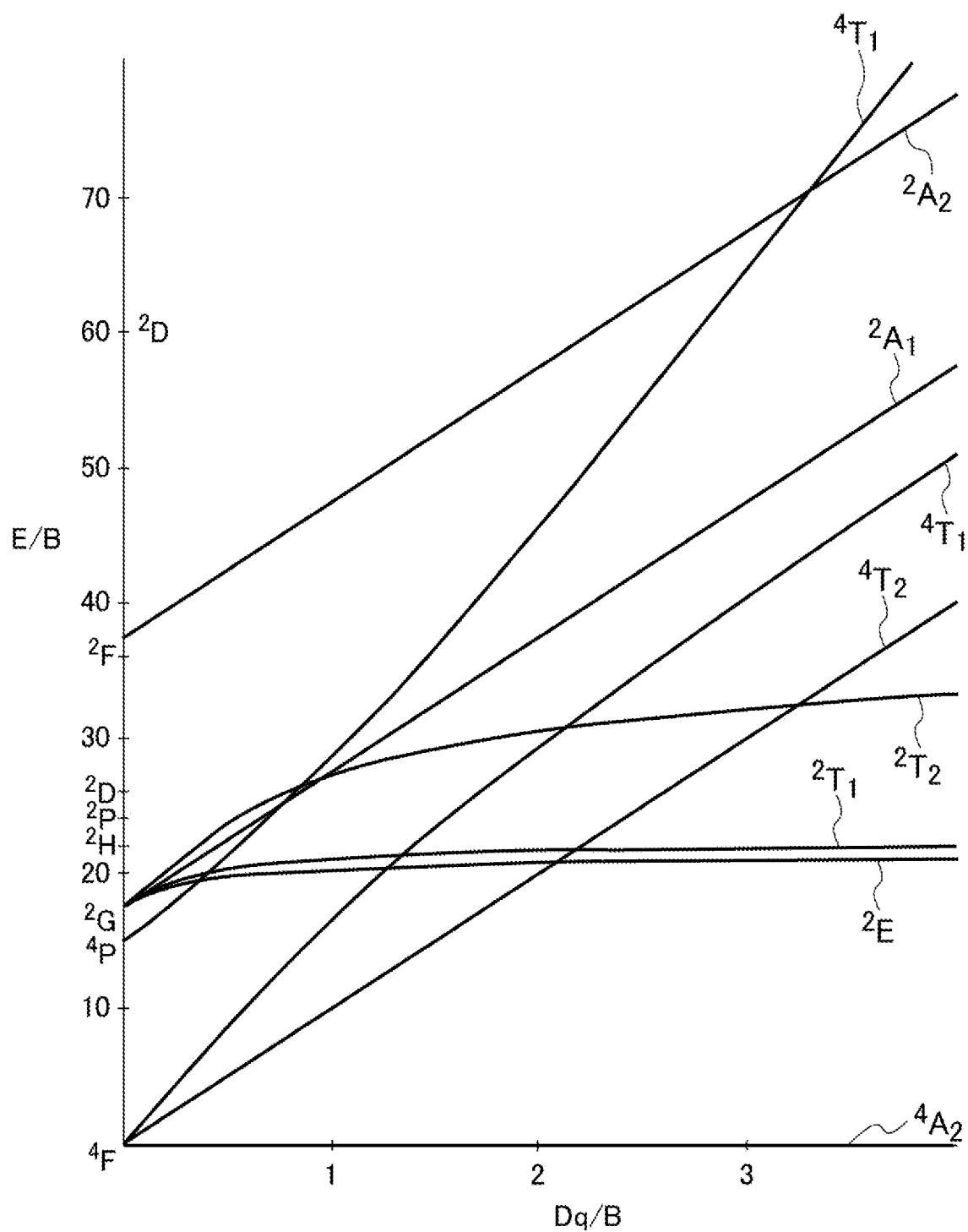
FIG. 5 is a view illustrating electron energy levels of $Cr^{3+}$.

The electron energy transition of $Cr^{3+}$ will be described below. FIG. 5 is a view illustrating electron energy levels of $Cr^{3+}$. Specifically, FIG. 5 is a Tanabe-Sugano diagram applied to six-coordinated $Cr^{3+}$, Me and the like.

A horizontal axis of FIG. 5 represents a quotient obtained by dividing Dq by the Racah parameter B, in which Dq means a magnitude of ligand field splitting and the Racah parameter B means strength of electrostatic repulsive force that acts between electrons. The horizontal axis of FIG. 5 can be understood as an index that indicates strength of the ligand field which $Cr^{3+}$ receives from the surrounding ligands in a crystal. Oxygen ions and the like are mentioned as the ligands around $Cr^{3+}$ in the crystal.

A vertical axis of FIG. 5 represents a quotient obtained by dividing energy E by the above-described Racah parameter B, in which the energy E means the energy from a ground state. The vertical axis of FIG. 5 can be understood as an index that indicates a magnitude of electron energy in an excited state formed by three 3d electrons which form an outermost electron cloud of $Cr^{3+}$, that is, an energy difference between the excited state and the ground state, which are formed by the three 3d electrons.

In accordance with FIG. 5, it can be seen that the electron energy in the excited state formed by the electrons on the 3d orbit of $Cr^{3+}$ in the phosphor crystal takes some discrete states. Moreover, in accordance with FIG. 5, it can be seen that the state of the electron energy, which is formed by the electrons owned by $Cr^{3+}$ in the phosphor crystal, changes by being affected by the type, number and arrangement manner of the surrounding ligands, distances thereof to the ligands, and the like, and as a result, the energy difference between the excited state and the ground state changes. Furthermore, in accordance with FIG. 5, it can be seen that each electron energy in the above-described excited state, which takes some discrete states, exhibits different behaviors depending on the ligand fields. Note that symbols such as $^2E$, $^4T_2$ and $^4A_2$, which are shown in FIG. 5, are well-known symbols each of which indicates the state of the discrete electron energy, which is formed by the three electrons on the 3d orbit of $Cr^{3+}$.

Here, the electron energy transition accompanied by the fluorescence usually becomes electron energy transition from a lowest excited state ($^2T_1$ and $^2E$ or $^4T_2$ in FIG. 5) to the ground state ($^4A_2$ in FIG. 5). Therefore, in accordance with FIG. 5, it can be seen that, when the strength of the ligand field which $Cr^{3+}$ receives in the crystal is strong (when a numeric value of the horizontal axis in FIG. 5 is large), $Cr^{3+}$ exhibits fluorescence by electron energy transition from $^2T_1$ and $^2E$ to $^4A_2$. Moreover, in accordance with FIG. 5, it can be seen that, when the strength of the ligand field is weak (when the numeric value of the horizontal axis in FIG. 5 is small), $Cr^{3+}$ exhibits fluorescence by electron energy transition from $^4T_2$ to $^4A_2$. The first phosphor 4 exhibits the fluorescence by the latter electron energy transition.

Note that, as seen from FIG. 5, in the electron energy transition from $^2T_1$ and $^2E$ to $^4A_2$, a fluorescence spectrum thereof becomes linear since the energy difference does not largely change even if the strength of the ligand field changes.

Meanwhile, as seen from FIG. 5, in the electron energy transition from $^4T_2$ to $^4A_2$, a fluorescence spectrum thereof becomes broad since the energy difference largely changes if the strength of the ligand field changes. The fluorescence spectrum of the first phosphor 4 becomes broad since this fluorescence spectrum is based on the electron energy transition (spin-allowed transition) from $^4T_2$ and $^4A_2$.

Note that, since energy transition between energy levels in the electron energy transition from $^2T_1$ and $^2E$ to $^4A_2$ in the 3d electrons of $Cr^{3+}$ is parity-forbidden transition, an afterglow time of the fluorescence is as long as 100 μs or more and less than 50 ms. This afterglow time of the fluorescence based on $Cr^{3+}$ becomes longer than an afterglow time (10 μs or less) of the fluorescence of $Ce^{3+}$ or $Eu^{2+}$ which exhibits the parity-allowed transition. However, since the electron energy transition from $^4T_2$ to $^4A_2$ in $Cr^{3+}$ is spin-allowed transition made between two states having the same spin, an afterglow time becomes as relatively short as approximately 100 μs.

A $Cr^{3+}$-activated phosphor that exhibits the fluorescence by the parity-forbidden (spin-allowed) electron energy transition as described above exhibits much longer afterglow properties than an $Eu^{2+}$-activated phosphor that exhibits fluorescence by parity-allowed electron energy transition. The present disclosure has been able to be achieved by finding that the $Ce^{3+}$-activated phosphor that exhibits the fluorescence by the parity-forbidden electron energy transition has surprisingly small saturation of the fluorescence output though exhibits much longer afterglow properties than the $Eu^{2+}$-activated phosphor.

Since the first wavelength-converted light 7 is such fluorescence based on the spin-allowed electron energy transition of $Cr^{3+}$, the first phosphor 4 radiates fluorescence that meets at least one of the following properties (A) to (D). As the first wavelength-converted light 7, fluorescence that meets two or more of the properties (A) to (D) may be radiated.

[Properties (A)]

The properties (A) are properties that the fluorescence spectrum of the first wavelength-converted light 7 has a maximum fluorescence intensity value in a region of a wavelength exceeding 710 nm. Here, the maximum fluorescence intensity value means a maximum fluorescence intensity of a peak in which fluorescence intensity exhibits a maximum value among peaks in a fluorescence spectrum. The fluorescence spectrum of the first wavelength-converted light 7 has the maximum fluorescence intensity value in a region of a wavelength preferably exceeding 730 nm, more preferably exceeding 750 nm.

In accordance with a light-emitting device in which the fluorescence spectrum of the first wavelength-converted light 7 has the maximum fluorescence intensity value in the region of the wavelength exceeding 710 nm, that is, the properties (A) are met, a point light source including a large amount of the near-infrared component can be easily obtained.

Moreover, the light-emitting device that meets the properties (A) is suitable as a medical light-emitting device since the fluorescence spectrum of the first wavelength-converted light 7 has the maximum fluorescence intensity value in the region of the wavelength exceeding 710 nm, which is such a wavelength region suitable for medial use.

[Properties (B)]

The properties (B) are properties that an 80% spectrum width in such a maximum fluorescence intensity value peak of the first wavelength-converted light 7 is 20 nm or more and less than 80 nm. Here, the 80% spectrum width in the maximum fluorescence intensity value peak means a spectrum width at an 80% intensity of the light emission peak intensity (maximum fluorescence intensity value) in the maximum fluorescence intensity value peak having the maximum fluorescence intensity value among the peaks of the fluorescence spectrum of the first wavelength-converted light 7. The above-described 80% spectrum width is preferably 25 nm or more and less than 70 nm, more preferably 30 nm or more and less than 65 nm.

When the above-described 80% spectrum width is within the above-described range, a fluorescent drug or a photosensitive drug can be used without being affected by variations of wavelength dependency of sensitivity of the above-described drug in the fluorescence imaging method and the photodynamic therapy (PDT). Here, the photosensitive drug means a drug with photosensitivity. In accordance with a light-emitting device that meets the properties (B), even if the wavelength dependency of the sensitivity has variations in the fluorescent drug or the photosensitive drug, it becomes possible to radiate high-output near-infrared rays capable of causing the above-described drug to sufficiently function without being affected by the variations.

[Properties (C)]

The properties (C) are properties that a ratio of the fluorescence intensity of the fluorescence spectrum of the first wavelength-converted light 7 at a wavelength of 780 nm with respect to the maximum fluorescence intensity value thereof exceeds 30%. Hereinafter, the above-described ratio the fluorescence intensity will also be referred to as "780 nm fluorescence intensity ratio." The 780 nm fluorescence intensity ratio preferably exceeds 60%, more preferably exceeds 80%.

When the 780 nm fluorescence intensity ratio is within the above-described range, the first wavelength-converted light 7 includes a large amount of a fluorescent component in the near-infrared wavelength range (650 to 1000 nm) in which light is easy to penetrate a living body, the wavelength range being called "biological window." Therefore, in accordance with the light-emitting device that meets the properties (C), the intensity of the near-infrared light that penetrates a living body can be increased.

[Properties (D)]

The properties (D) are properties that a $1/10$ afterglow of the first wavelength-converted light 7 is less than 1 ms. Here, the $1/10$ afterglow means a time $\tau_{1/10}$ taken from a time when the maximum light emission intensity is exhibited until a time when the intensity decreases to $1/10$ of the maximum light emission intensity. The $1/10$ afterglow is preferably 10 μs or more and less than 1 ms, more preferably 10 μs or more and less than 800 μs, still more preferably 10 μs or more and less than 400 μs, particularly preferably 10 μs or more and less than 350 μs, more particularly preferably 10 μs or more and less than 100 μs.

If the $1/10$ afterglow is within the above-described range, even when the light density of the excitation light that excites the first phosphor 4 is high, the output of the fluorescence emitted by the first phosphor 4 becomes less likely to saturate. Therefore, in accordance with the light-emitting device that meets the properties (D), it becomes possible to radiate the high-output near-infrared light in which the saturation of the output of the fluorescence is low when laser light with a high light density is applied.

Note that the $1/10$ afterglow of the first wavelength-converted light 7 becomes longer than a $1/10$ afterglow of the short afterglow (less than 10 μs) fluorescence based on the parity-allowed transition of $Ce^{3+}$, $Eu^{2+}$ or the like. This is because the first wavelength-converted light 7 is fluorescence based on the spin-allowed electron energy transition of $Cr^{3+}$ with a relatively long afterglow.

As the first phosphor 4, for example, there can be used a phosphor such as $Lu_2CaMg_2(SiO_4)_3:Cr^{3+}$, $Y_3Ga_2(AlO_4)_3:Cr^{3+}$, $Y_3Ga_2(GaO_4)_3:Cr^{3+}$, $Gd_3Ga_2(AlO_4)_3:Cr^{3+}$, $Gd_3Ga_2(GaO_4)_3:Cr^{3+}$, $(Y,La)_3Ga_2(GaO_4)_3:Cr^{3+}$, $(Gd,La)_3Ga_2(GaO_4)_3:Cr^{3+}$, $Ca_2LuZr_2(AlO_4)_3:Cr^{3+}$, $Ca_2GdZr_2(AlO_4)_3:Cr^{3+}$, $Lu_3Sc_2(GaO_4)_3:Cr^{3+}$, $Y_3Sc_2(AlO_4)_3:Cr^{3+}$, $Y_3Sc_2(GaO_4)_3:Cr^{3+}$, $Gd_3Sc_2(GaO_4)_3:Cr^{3+}$, $La_3Sc_2(GaO_4)_3:Cr^{3+}$, $Ca_3Sc_2(SiO_4)_3:Cr^{3+}$, $Ca_3Sc_2(GeO_4)_3:Cr^{3+}$, $BeAl_2O_4:Cr^{3+}$, $LiAl_5O_8:Cr^{3+}$, $LiGa_5O_8:Cr^{3+}$, $Mg_2SiO_4:Cr^{3+},Li^+$, $La_3Ga_5GeO_{14}:Cr^{3+}$, and $La_3Ga_{5.5}Nb_{0.5}O_{14}:Cr^{3+}$.

It is preferable that the first phosphor 4 be composed of ceramics. When the first phosphor 4 is composed of ceramics, heat dissipation of the first phosphor 4 increases, and accordingly, a decrease of the output of the first phosphor 4 due to temperature quenching is suppressed, whereby the light-emitting device becomes able to radiate the high-output near-infrared light.

In the light-emitting device 1, the first wavelength-converted light 7 radiated by the first phosphor 4 has a specific fluorescent component based on the electron energy transition of $Cr^{3+}$. Thus, in accordance with the light-emitting device 1, such a fluorescent drug as ICG and such a photosensitive drug (also a photosensitive drug) as phthalocyanine can be excited efficiently.

The first wavelength-converted light 7 has a light component preferably across the whole of a wavelength range of 700 nm or more and less than 800 nm, more preferably across the whole of a wavelength range of 750 nm or more and less than 800 nm. Thus, the fluorescent drug and the photosensitive drug can more efficiently absorb the light component in the near-infrared range, which is radiated by the first phosphor 4, thus making it possible to increase a light quantity of the near-infrared light radiated from the fluorescent drug and a heat ray radiated from the photosensitive drug. Therefore, when the first wavelength-converted light 7 has a light component across the whole of the wavelength range of 700 nm or more and less than 800 nm, there increase the light quantity of the near-infrared light radiated from the fluorescent drug and the heat ray radiated from the photosensitive drug, and the light-emitting device suitable for medical use can be obtained.

Note that, preferably, the fluorescence spectrum of the first wavelength-converted light 7 does not include a trail of the linear spectral component, which is derived from the electron energy transition of $Cr^{3+}$. The linear spectral component derived from the electron energy transition of $Cr^{3+}$ is long-afterglow fluorescent component due to the spin-forbidden transition of $Cr^{3+}$. When the fluorescence spectrum of the first wavelength-converted light 7 does not include the above-described trail, the first wavelength-converted light 7 does not include the long-afterglow fluorescent component due to the spin-forbidden transition of $Cr^{3+}$, and accordingly, a high-output point light source can be obtained, in which the saturation of the fluorescence output when the laser light with a high light density is applied is smaller.

The wavelength converter 3 includes, as a phosphor, only the first phosphor 4 including the fluorescence based on the electron energy transition of $Cr^{3+}$. Moreover, the first phosphor 4 does not include an activator other than $Cr^{3+}$. Therefore, light absorbed by the first phosphor 4 is converted into only the fluorescence based on the electron energy transition of $Cr^{3+}$. Hence, in accordance with the light-emitting device 1 in which the first phosphor 4 does not include an activator other than $Cr^{3+}$, design of the output light, which maximizes the output ratio of the near-infrared fluorescent component, is facilitated.

It is preferable that the first phosphor 4 have a crystal structure of garnet. It is easy to modify a composition of the garnet phosphor, and accordingly, the garnet phosphor is capable of preparing a large number of phosphor compounds. Therefore, when the first phosphor 4 has a crystal structure of garnet, it is easy to adjust a crystal field around $Cr^{3+}$, and color tone control of the fluorescence based on the electron energy transition of $Cr^{3+}$ is facilitated.

Note that phosphors having such a garnet structure, and particularly oxides having the same have a polyhedral particle shape close to a sphere, and are excellent in dispersibility for a group of phosphor particles. Therefore, when the first phosphor 4 has the garnet structure, the wavelength converter 3 excellent in light transparency can be produced relatively easily, and it becomes possible to increase the output of the light-emitting device 1. Moreover, since the phosphors having the crystal structure of garnet have been actually used as phosphors for LED, the light-emitting device 1 in which the first phosphor 4 has the crystal structure of garnet increases reliability thereof.

The first phosphor 4 is preferably an oxide-based phosphor, more preferably an oxide phosphor. Note that the oxide-based phosphor refers to a phosphor that does not include nitrogen but includes oxygen.

Oxides are stable substances in the atmosphere, and accordingly, when such oxide phosphors generate heat due to high-density photoexcitation by laser light, a quality degradation of phosphor crystals, which may be caused by oxidation in the atmosphere, is less likely to occur as compared with nitride phosphors. When the first phosphor 4 is entirely an oxide-based phosphor, the light-emitting device 1 with high reliability can be obtained.

Note that the first phosphor 4 may include two or more types of the $Cr^{3+}$-activated phosphor. When the first phosphor 4 includes two or more types of the $Cr^{3+}$-activated phosphor, at least an output light component in the near-infrared wavelength region can be controlled. Therefore, in accordance with the light-emitting device in which the first phosphor 4 includes two or more types of the $Cr^{3+}$-activated phosphor, it becomes easy to adjust a spectral distribution of the near-infrared fluorescent component.

<Sealing Material>

In the wavelength converter 3, the first phosphor 4 is included in the sealing material 5. Preferably, the first phosphor 4 is dispersed in the sealing material 5. When the first phosphor 4 is dispersed in the sealing material 5, it becomes possible to efficiently absorb the primary light 6 radiated by the light source 2, and to efficiently perform wavelength conversion for the primary light 6 into the near-infrared light. Moreover, when the first phosphor 4 is dispersed in the sealing material 5, the wavelength converter 3 is easily formed into a sheet shape or a film shape.

The sealing material 5 is composed of at least one of an organic material and an inorganic material. The sealing material 5 is preferably composed of at least one of a transparent (translucent) organic material and a transparent (translucent) inorganic material. As such a sealing material composed of the organic material, for example, a transparent organic material such as a silicon resin is mentioned. As such a sealing material composed of the inorganic material, for example, a transparent inorganic material such as low-melting-point glass is mentioned.

Note that, preferably, the wavelength converter 3 is composed of an inorganic material. Here, the inorganic material means a material other than organic materials, and is a concept involving ceramics and metals. The wavelength converter 3 is composed of an inorganic material, whereby thermal conductivity thereof increases as compared with a wavelength converter including an organic material such as a sealing resin, and accordingly, heat dissipation design can be easily prepared. Therefore, even if the first phosphor 4 is subjected to high-density photoexcitation by the primary light 6 radiated from the light source 2, a temperature rise of the wavelength converter 3 can be suppressed effectively. As a result, temperature quenching of the first phosphor 4 in the wavelength converter 3 is suppressed, and it becomes possible to increase the output of the light emission.

When the wavelength converter 3 is composed of an inorganic material, the sealing material 5 is preferably composed of an inorganic material. Moreover, zinc oxide (ZnO) is preferable as the inorganic material for the sealing material 5. When the sealing material 5 is composed of an inorganic material, heat dissipation of the first phosphor 4 further increases, and accordingly, a decrease of the output of the first phosphor 4 due to temperature quenching is suppressed, and it becomes possible to radiate the high-output near-infrared light.

Note that, as a modified example of the light-emitting device 1, a wavelength converter that not include the sealing material 5 can be adopted in place of the wavelength converter 3. In this case, particles of the first phosphor 4 are only required to be adhered to one another by using an organic or inorganic binding agent. Moreover, the particles of the first phosphor 4 can also be adhered to one another by using a heating reaction of the first phosphor 4. As the binding agent, there can be used a resin-based adhesive used commonly, or ceramic fine particles, low-melting-point glass or the like. In accordance with the wavelength converter that does not include the sealing material 5, the thickness of the wavelength converter can be thinned.

(Functions)

A description will be given of functions of the light-emitting device 1. First, the primary light 6 (laser light) radiated from the light source 2 is applied to the front surface 3a of the wavelength converter 3. The applied primary light 6 penetrates the wavelength converter 3. Then, when the primary light 6 penetrates the wavelength converter 3, the first phosphor 4 included in the wavelength converter 3 absorbs a part of the primary light 6 and radiates the first wavelength-converted light 7. As described above, light including the primary light 6 and the first wavelength-converted light 7 is radiated as output light from the back surface 3b of the wavelength converter 3.

The light-emitting device 1 radiates the first wavelength-converted light 7 having a specific fluorescent component including a large amount of the near-infrared fluorescent component based on the electron energy transition of $Cr^{3+}$, and therefore, becomes suitable as a medical near-infrared light source or a sensing near-infrared light source.

The light-emitting device 1 can be used as an illuminating device for a medical light source or a medical illuminating device. Moreover, particularly, the light-emitting device 1 can be used as an illuminating device for a medical system using the fluorescence imaging method or the photodynamic therapy. Note that, since such a medical system is a medical system that uses a fluorescent drug, the light-emitting device 1 for the above-described medical system can also be said to be a light-emitting device for the medical system that uses the fluorescent drug.

The light-emitting device 1 as an illuminating device for the medical light source or the medical illuminating device becomes a light source or an illuminating device, which irradiates an inside of a living body through "biological window" with broad near-infrared high-output light, and can cause such a fluorescent or photosensitive drug taken into the living body to sufficiently function. Therefore, in accordance with the light-emitting device 1 as the illuminating device for the medical light source or the medical illuminating device, and particularly as such an illuminating device for the medical system using the fluorescence imaging method or the photodynamic therapy, a light-emitting device for which a large therapeutic effect can be expected can be obtained.

The light-emitting device 1 can also be used as a light source for a sensing system or an illuminating system for a sensing system. In the light-emitting device 1, a high-sensitivity sensing system can be configured by using an orthodox light receiving element having photosensitivity in the near-infrared wavelength region. Therefore, in accordance with the light-emitting device 1 as the light source for the sensing system or the illuminating system for the sensing system, a light-emitting device can be obtained, in which miniaturization of the sensing system and extension of a sensing range are facilitated.

Second Embodiment

A light-emitting device 1A according to a second embodiment will be described. The light-emitting device 1A according to the second embodiment uses the wavelength converter 3A in place of the wavelength converter 3 of the light-emitting device 1 according to the first embodiment. A different point between the light-emitting device 1A according to the second embodiment and the light-emitting device 1 according to the first embodiment is only the wavelength converter 3A. Therefore, the wavelength converter 3A will be described below, and regarding other members, a description of configurations and functions thereof will be omitted or simplified below.

(Wavelength Converter)

The wavelength converter 3A includes, the first phosphor 4, a second phosphor 8, and the sealing material 5. In the wavelength converter 3A, the first phosphor 4 and the second phosphor 8 are included in the sealing material 5. That is, the wavelength converter 3A of the light-emitting device 1A further includes the second phosphor 8 that absorbs the primary light 6 and converts the primary light 6 into second wavelength-converted light 9 that has a longer wavelength than the primary light 6 and is different from the first wavelength-converted light 7.

The wavelength converter 3A is the same as the wavelength converter 3 of the light-emitting device 1 according to the first embodiment except that the wavelength converter 3A further includes the second phosphor 8. Therefore, the second phosphor 8 will be described below, and a description of configurations and functions of others will be omitted or simplified below.

<Second Phosphor>

The second phosphor 8 is such a phosphor that absorbs the primary light 6 and converts the primary light 6 into the second wavelength-converted light 9 that has a longer wavelength than the primary light 6 and is different from the first wavelength-converted light 7. The wavelength converter 3A further includes the second phosphor 8 in addition to the first phosphor 4, whereby the light-emitting device 1A is enabled to radiate white output light by additive color mixture with the primary light 6 emitted by the light source 2, for example, with blue laser light.

When the wavelength converter 3A further includes the second phosphor 8 in addition to the first phosphor 4 as described above, it is made possible to control the shape and excitation properties of the fluorescence spectrum radiated from the wavelength converter 3A. Therefore, the obtained light-emitting device 1A becomes able to easily adjust a spectral distribution of the output light according to the purpose of use.

The second phosphor 8 included in the wavelength converter 3A is not particularly limited as long as being capable of absorbing the primary light 6 emitted by the light source 2 and radiating the second wavelength-converted light 9 that is visible light. Preferably, the second phosphor 8 is a $Ce^{3+}$-activated phosphor having a matrix crystal composed of a compound containing at least one selected from the group of compounds consisting of a garnet type compound, a calcium ferrite type compound, and a lanthanum silicon nitride ($La_3Si_6N_{11}$) type compound, as a main component. Moreover, preferably, the second phosphor 8 is a $Ce^{3+}$-activated phosphor having the matrix crystal composed of a compound containing at least one selected from the group of the compounds consisting of the garnet type compound, the calcium ferrite type compound, and the lanthanum silicon nitride ($La_3Si_6N_{11}$) type compound. When such a second phosphor 8 as described above is used, it becomes possible to obtain output light that has a large quantity of green to yellow-series light components.

As the second phosphor 8, for example, there is used a $Ce^{3+}$-activated phosphor having the matrix crystal composed of a compound (B) containing at least one selected from the group consisting of $M_3RE_2(SiO_4)_3$, $RE_3Al_2(AlO_4)_3$, $MRE_2O_4$, and $RE_3Si_6N_{11}$, as a main component. Moreover, as the second phosphor 8, for example, there is used a $Ce^{3+}$-activated phosphor having the matrix crystal composed of a compound containing at least one selected from the group consisting of $M_3RE_2(SiO_4)_3$, $RE_3Al_2(AlO_4)_3$, $MRE_2O_4$, and $RE_3Si_6N_{11}$. Preferably, the second phosphor 8 a $Ce^{3+}$-activated phosphor having the matrix crystal composed of a solid solution containing the above-described compound (B) as an end member. Note that, in the above-described compound (B), M is alkaline earth metal, and RE is a rare earth element.

Each of these second phosphors 8 absorbs light within a wavelength range of 430 nm or more and 480 nm or less well, and highly efficiently converts the absorbed light into green to yellow-series light having a maximum intensity value within a wavelength range of 540 nm or more and less than 590 nm. Therefore, the light source 2 is set to radiate cold color light as the primary light 6, and then the above-described second phosphor 8 is used, thus making it possible to easily obtain the visible light component.

When the wavelength converter 3A includes the first phosphor 4 and the second phosphor 8, it is preferable that the first phosphor 4 emit the first wavelength-converted light 7 by absorbing at least either one of the primary light 6 emitted by the light source 2 and the second wavelength-converted light 9 emitted by the second phosphor 8. As mentioned above, it is preferable that the first phosphor 4 be a phosphor that absorbs the primary light 6 emitted by the light source 2 and radiates the first wavelength-converted light 7 that is near-infrared light.

The first phosphor 4 may be a phosphor that absorbs the second wavelength-converted light 9 emitted by the second phosphor 8 and radiates the first wavelength-converted light 7 that is near-infrared light. That is, the second phosphor 8 may be excited by the primary light 6 to radiate the second wavelength-converted light 9, and the first phosphor 4 may be excited by the second wavelength-converted light 9 to radiate the first wavelength-converted light 7. In this case, even if the first phosphor 4 is a phosphor that is hardly excited by the primary light 6, interposition of the second phosphor 8 makes it possible to excite the first phosphor 4 by the fluorescence emitted by the second phosphor 8.

Therefore, when the first phosphor 4 absorbs the second wavelength-converted light 9 and radiates the first wavelength-converted light 7, a phosphor that absorbs visible light is made capable of being selected as the first phosphor 4, and accordingly, options of the first phosphor 4 are expanded, and it becomes easy to industrially produce the light-emitting device 1A. Moreover, when the first phosphor 4 absorbs the second wavelength-converted light 9 and radiates the first wavelength-converted light 7, the light-emitting device 1A becomes able to radiate the first wavelength-converted light 7 in which a light component intensity of the near-infrared light is large.

Note that the second phosphor 8 may include two or more types of the $Cr^{3+}$-activated phosphor. When the second phosphor 8 includes two or more types of the $Cr^{3+}$-activated phosphor, at least the output light component in the near-infrared wavelength region can be controlled, and accordingly, it becomes easy to adjust the spectral distribution of the near-infrared fluorescent component.

(Functions)

A description will be given of functions of the light-emitting device 1A. First, the primary light 6 (laser light) radiated from the light source 2 is applied to the front surface 3a of the wavelength converter 3A. The applied primary light 6 penetrates the wavelength converter 3A. Then, when the primary light 6 penetrates the wavelength converter 3A, the second phosphor 8 included in the wavelength converter 3A absorbs a part of the primary light 6 and radiates the second wavelength-converted light 9. Moreover, the first phosphor 4 included in the wavelength converter 3A absorbs a part of the primary light 6 and/or the second wavelength-converted light 9 and radiates the first wavelength-converted light 7. As described above, light including the primary light 6, the first wavelength-converted light 7, and the second wavelength-converted light 9 is radiated as output light from the back surface 3b of the wavelength converter 3A.

The light-emitting device 1A radiates the first wavelength-converted light 7 having a specific fluorescent component including a large amount of the near-infrared fluorescent component based on the electron energy transition of $Cr^{3+}$, and therefore, becomes suitable as a medical near-infrared light source or a sensing near-infrared light source.

The light-emitting device 1A can be used as an illuminating device for a medical light source or a medical illuminating device. Moreover, particularly, the light-emitting device 1A can be used as an illuminating device for a medical system using the fluorescence imaging method or the photodynamic therapy. Note that, since such a medical system is a medical system that uses a fluorescent drug or a photosensitive drug, the light-emitting device 1A for the above-described medical system can also be said to be a light-emitting device for the medical system that uses the fluorescent drug or the photosensitive drug.

The light-emitting device 1A becomes a light source or an illuminating device, which irradiates an inside of a living body through "biological window" with broad near-infrared high-output light, and can cause such a fluorescent or photosensitive drug taken into the living body to sufficiently function. Therefore, in accordance with the light-emitting device 1A, a light-emitting device for which a large therapeutic effect can be expected can be obtained.

The light-emitting device 1A can also be used as a light source for a sensing system or an illuminating system for a sensing system. In the light-emitting device 1A, a high-sensitivity sensing system can be configured by using an orthodox light receiving element having photosensitivity in the near-infrared wavelength region. Therefore, in accordance with the light-emitting device 1A, a light-emitting device can be obtained, in which miniaturization of the sensing system and extension of a sensing range are facilitated.

Third Embodiment

A light-emitting device 1B according to a third embodiment will be described. The light-emitting device 1B according to the third embodiment uses the wavelength converter 3B in place of the wavelength converter 3 of the light-emitting device 1 according to the first embodiment. A different point between the light-emitting device 1B according to the third embodiment and the light-emitting device 1 according to the first embodiment is only the wavelength converter 3B. Therefore, the wavelength converter 3B will be described below, and regarding other members, a description of configurations and functions thereof will be omitted or simplified below.

(Wavelength Converter)

The wavelength converter 3B includes the first phosphor 4 and the sealing material 5. In the wavelength converter 3B, the first phosphor 4 is included in the sealing material 5. The wavelength converter 3B is the same as the wavelength converter 3 of the light-emitting device 1 according to the first embodiment in terms of including the first phosphor 4 and the sealing material 5; however, is different from the wavelength converter 3 in terms of optical functions.

In the wavelength converter 3 of the light-emitting device 1 according to the first embodiment, the primary light 6 applied to the wavelength converter 3 penetrates the wavelength converter 3. Meanwhile, in the wavelength converter 3B, much of the primary light 6 applied to the wavelength converter 3B enters the inside of the wavelength converter 3B from the front surface 3a of the wavelength converter 3B, and the rest thereof is reflected on the front surface 3a.

The wavelength converter 3B is configured so that irradiation light of the primary light 6 (laser light) enters the wavelength converter 3B from the front surface 3a of the wavelength converter 3B, and that output light of the first phosphor 4 is radiated from the front surface 3a of the wavelength converter 3B. Thus, much of the primary light 6 applied to the wavelength converter 3B enters the inside of the wavelength converter 3B from the front surface 3a of the wavelength converter 3B, and the rest thereof is reflected on the front surface 3a.

(Functions)

A description will be given of functions of the light-emitting device 1B. First, the primary light 6 (laser light) radiated from the light source 2 is applied to the front surface 3a of the wavelength converter 3B. Much of the primary light 6 enters the inside of the wavelength converter 3B from the front surface 3a of the wavelength converter 3B, and the rest thereof is reflected on the front surface 3a. In the wavelength converter 3B, the first wavelength-converted light 7 is radiated from the first phosphor 4 excited by the primary light 6, and the first wavelength-converted light 7 is radiated from the front surface 3a.

The light-emitting device 1B radiates the first wavelength-converted light 7 having a specific fluorescent component including a large amount of the near-infrared fluorescent component based on the electron energy transition of $Cr^{3+}$, and therefore, becomes suitable as a medical near-infrared light source or a sensing near-infrared light source.

The light-emitting device 1B can be used as an illuminating device for a medical light source or a medical illuminating device. Moreover, particularly, the light-emitting device 1B can be used as an illuminating device for a medical system using the fluorescence imaging method or the photodynamic therapy. Note that, since such a medical system is a medical system that uses a fluorescent drug or a photosensitive drug, the light-emitting device 1B for the above-described medical system can also be said to be a light-emitting device for the medical system that uses the fluorescent drug or the photosensitive drug.

The light-emitting device 1B becomes a light source or an illuminating device, which irradiates an inside of a living body through "biological window" with broad near-infrared high-output light, and can cause such a fluorescent or photosensitive drug taken into the living body to sufficiently function. Therefore, in accordance with the light-emitting device 1B, a light-emitting device for which a large therapeutic effect can be expected can be obtained.

The light-emitting device 1B can also be used as a light source for a sensing system or an illuminating system for a sensing system. In the light-emitting device 1B, a high-sensitivity sensing system can be configured by using an orthodox light receiving element having photosensitivity in the near-infrared wavelength region. Therefore, in accordance with the light-emitting device 1B, a light-emitting device can be obtained, in which miniaturization of the sensing system and extension of a sensing range are facilitated.

Fourth Embodiment

A light-emitting device 1C according to a fourth embodiment will be described. The light-emitting device 1C according to the fourth embodiment uses the wavelength converter 3C in place of the wavelength converter 3A of the light-emitting device 1A according to the second embodiment. A different point between the light-emitting device 1C according to the fourth embodiment and the light-emitting device 1A according to the second embodiment is only the wavelength converter 3C. Therefore, the wavelength converter 3C will be described below, and regarding other members, a description of configurations and functions thereof will be omitted or simplified below.

(Wavelength Converter)

The wavelength converter 3C includes, the first phosphor 4, the second phosphor 8, and the sealing material 5. In the wavelength converter 3C, the first phosphor 4 and the second phosphor 8 are included in the sealing material 5. That is, the wavelength converter 3C of the light-emitting device 1C further includes the second phosphor 8 that absorbs the primary light 6 and converts the primary light 6 into second wavelength-converted light 9 that has a longer wavelength than the primary light 6 and is different from the first wavelength-converted light 7. The wavelength converter 3C is the same as the wavelength converter 3A of the light-emitting device 1A according to the second embodiment in terms of including the first phosphor 4, the second phosphor 8 and the sealing material 5; however, is different from the wavelength converter 3A in terms of optical functions.

The second phosphor 8 for use in the wavelength converter 3C is the same as that in the wavelength converter 3A of the light-emitting device 1A according to the second embodiment, and accordingly, a description thereof will be omitted. The wavelength converter 3C further includes the second phosphor 8, whereby the light-emitting device 1C is enabled to radiate white output light by additive color mixture with the primary light 6 emitted by the light source 2, for example, with blue laser light.

When the first phosphor 4 and the second phosphor 8 are used in appropriate combination with each other, it becomes possible to control the shape and excitation properties of the fluorescence spectrum of the first wavelength-converted light 7. Therefore, the obtained light-emitting device C becomes able to easily adjust the spectral distribution of the output light according to the purpose of use.

In the wavelength converter 3A of the light-emitting device 1 according to the second embodiment, the primary light 6 applied to the wavelength converter 3A penetrates the wavelength converter 3. Meanwhile, in the wavelength converter 3C, much of the primary light 6 applied to the wavelength converter 3C enters the inside of the wavelength converter 3C from the front surface 3a of the wavelength converter 3C, and the rest thereof is reflected on the front surface 3a.

The wavelength converter 3C is configured so that irradiation light of the primary light 6 (laser light) enters the wavelength converter 3C from the front surface 3a of the wavelength converter 3B, and that output light of the first phosphor 4 is radiated from the front surface 3a of the wavelength converter 3B. Thus, much of the primary light 6 applied to the wavelength converter 3C enters the inside of the wavelength converter 3C from the front surface 3a of the wavelength converter 3C, and the rest thereof is reflected on the front surface 3a.

(Functions)

In the light-emitting device 1C illustrated in FIG. 4, first, the primary light 6 (laser light) radiated from the light source 2 is applied to the front surface 3a of the wavelength converter 3C. Much of the primary light 6 enters the inside of the wavelength converter 3C from the front surface 3a of the wavelength converter 3C, and the rest thereof is reflected on the front surface 3a. In the wavelength converter 3C, the second wavelength-converted light 9 is radiated from the second phosphor 8 excited by the primary light 6, and the first wavelength-converted light 7 is radiated from the first phosphor 4 excited by the primary light 6 and/or the second wavelength-converted light 9. Then, the first wavelength-converted light 7 and the second wavelength-converted light 9 are radiated from the front surface 3a.

The light-emitting device 1C radiates the first wavelength-converted light 7 having a specific fluorescent component including a large amount of the near-infrared fluorescent component based on the electron energy transition of $Cr^{3+}$, and therefore, becomes suitable as a medical near-infrared light source or a sensing near-infrared light source.

The light-emitting device 1C can be used as an illuminating device for a medical light source or a medical illuminating device. Moreover, particularly, the light-emitting device 1C can be used as an illuminating device for a medical system using the fluorescence imaging method or the photodynamic therapy. Note that, since such a medical system is a medical system that uses a fluorescent drug or a photosensitive drug, the light-emitting device 1C for the above-described medical system can also be said to be a light-emitting device for the medical system that uses the fluorescent drug or the photosensitive drug.

The light-emitting device 1C becomes a light source or an illuminating device, which irradiates an inside of a living body through "biological window" with broad near-infrared high-output light, and can cause such a fluorescent or photosensitive drug taken into the living body to sufficiently function. Therefore, in accordance with the light-emitting device 1C, a light-emitting device for which a large therapeutic effect can be expected can be obtained.

The light-emitting device 1C can also be used as a light source for a sensing system or an illuminating system for a sensing system. In the light-emitting device 1C, a high-sensitivity sensing system can be configured by using an orthodox light receiving element having photosensitivity in the near-infrared wavelength region. Therefore, in accordance with the light-emitting device 1C, a light-emitting device can be obtained, in which miniaturization of the sensing system and extension of a sensing range are facilitated.

[Electronic Device]

An electronic device according to this embodiment can be obtained by using any of the above-described light-emitting devices 1 to 1C. That is, the electronic device according to this embodiment includes any of the light-emitting devices 1 to 1C according to this embodiment. A large therapeutic effect can be expected for the light-emitting devices 1 to 1C, which easily achieves miniaturization of the sensing system, and the like. The electronic device according to this embodiment uses the light-emitting device according to this embodiment. Accordingly, when the electronic device according to this embodiment is used for a medical device or a sensing device, such a large therapeutic effect and miniaturization of the sensing system can be expected.

[Endoscope and Endoscope System]

An endoscope according to this embodiment includes the above-described medical light-emitting device. Examples of the endoscope according to this embodiment and an endoscope system using the endoscope will be described below with reference to FIG. 6 and FIG. 7. Note that the endoscope which will be described below is an example of including the light-emitting device 1A or 1C that radiates visible light in addition to near-infrared light.

(Endoscope)

Figure 6:
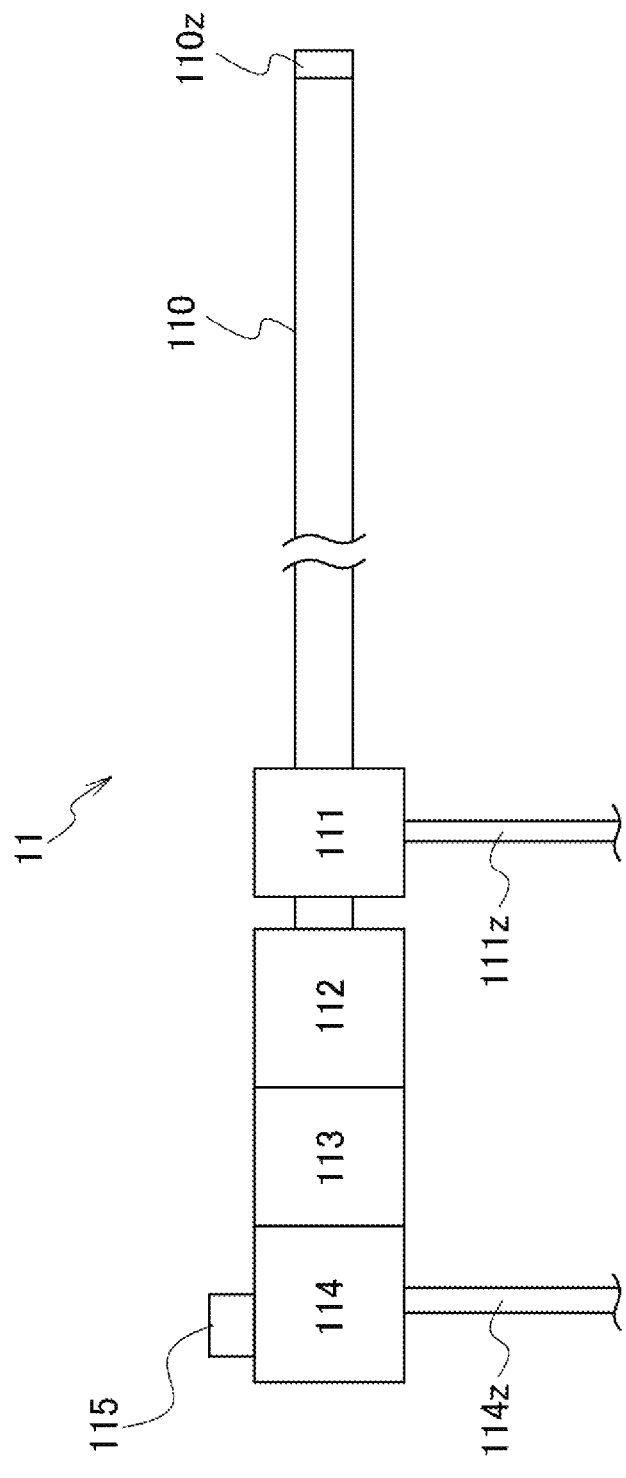
FIG. 6 is a diagram schematically illustrating a configuration of an endoscope according to an embodiment.

As illustrated in FIG. 6, the endoscope 11 includes a scope 110, a light source connector 111, a mount adapter 112, a relay lens 113, a camera head 114, and an operation switch 115.

The scope 110 is an elongated light guide member capable of guiding light from a terminal end thereof to a distal end thereof, and is inserted into a body at the time of use. The scope 110 includes an imaging window 110z on the distal end, and an optical material such as optical glass and optical plastics is used for the imaging window 110z. The scope 110 further includes an optical fiber that guides, to the distal end, light introduced from the light source connector 111, and an optical fiber through which an optical image incident from the imaging window 110z is to be transmitted.

The mount adapter 112 is a member for attaching the scope 110 to the camera head 114. A variety of the scopes 110 are freely detachably attached to the mount adapter 112.

From the light-emitting device 1A or 1C, the light source connector 111 introduces illumination light to be applied to the affected area and the like in the body. In this embodiment, the illumination light includes visible light and near-infrared light. The light introduced into the light source connector 111 is introduced via the optical fiber to the distal end of the scope 110, and is applied from the imaging window 110z to the affected area and the like in the body. Note that, as illustrated in FIG. 6, a transmission cable 111z for guiding the illumination light from the light-emitting device 1A or 1C to the scope 110 is connected to the light source connector 111. The transmission cable 111z may include the optical fiber.

The relay lens 113 converges an optical image, which is to be transferred through the scope 110, onto an imaging surface of an image sensor. Note that the relay lens 113 may adjust a focal point and a magnification by moving a lens in response to an operation amount of the operation switch 115.

The camera head 114 includes a color separation prism in an inside thereof. The color separation prism separates the light, which is converged by the relay lens 113, into four colors which are red light (R light), green light (G light), blue light (B light), and near-infrared light (IR light). The color separation prism is composed, for example, of a translucent member such as glass.

The camera head 114 further includes the image sensor as a detector in the inside. For example, four image sensors are provided, and the four image sensors convert optical images, which are individually formed on the imaging surfaces thereof, into electrical signals. The image sensors are not particularly limited; however, at least either one of charge coupled devices (CCDs) and complementary metal oxide semiconductors (CMOSs) can be used. The four image sensors are dedicated sensors which receive pieces of light of a near-infrared component (IR component), a blue component (B component), a red component (R component), and a green component (G component).

In place of the color separation prism, the camera head 114 may include a color filter in the inside. The color filter is provided on the imaging surfaces of the image sensors. For example, four color filters are provided, and the four color filters receive the light converged by the relay lens 113, and selectively allow penetration of the red light (R light), the green light (G light), the blue light (B light), and the near-infrared light (IR light).

It is preferable that the color filter that selectively allows penetration of the IR light be provided with a barrier film that cuts a reflection component of the near-infrared light (IR light), which is included in the illumination light. Thus, only the fluorescence emitted from the ICG and composed of the IR light will form an image on the imaging surface of the image sensor for the IR light. Therefore, it becomes easy to clearly observe an affected area that emits light by the ICG.

Note that, as illustrated in FIG. 6, to the camera head 114, connected is a signal cable 114z for transmitting the electrical signals, which are output from the image sensors, to a camera control unit (CCU) 12 to be described later.

In the endoscope 11 having such a configuration, light from the subject is guided to the relay lens 113 through the scope 110, and further, penetrates the color separation prism in the camera head 114, and forms images on the four image sensors.

(Endoscope System)

Figure 7:
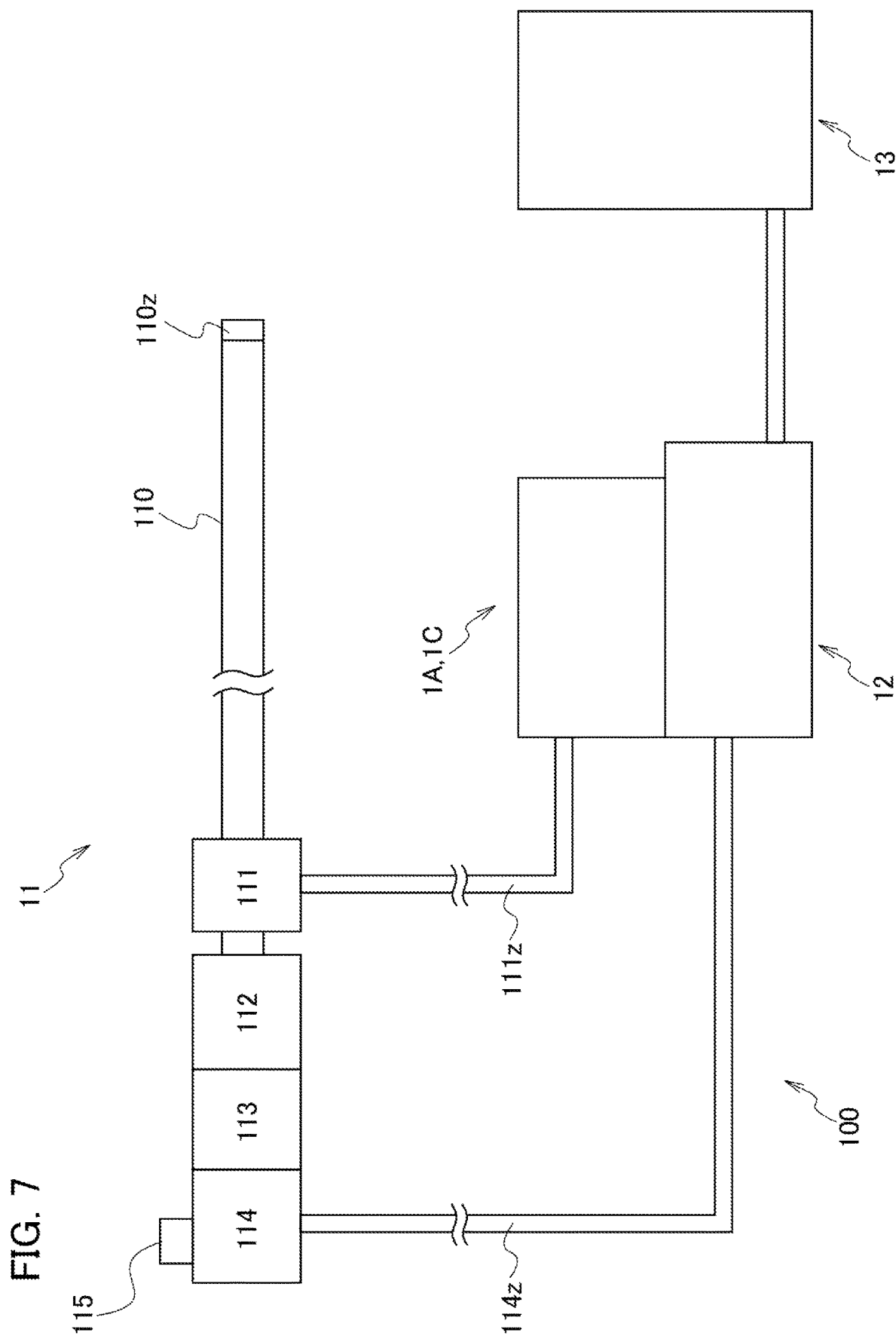
FIG. 7 is a diagram schematically illustrating a configuration of an endoscope system according to the embodiment.

As illustrated in FIG. 7, an endoscope system 100 includes the endoscope 11 that captures the inside of the subject, the camera control unit (CCU) 12, the light-emitting device 1A or 1C, and a display device 13 such as a display.

The CCU 12 includes at least an RGB signal processing unit, an IR signal processing unit, and an output unit. The CCU 12 executes a program held by a memory in the inside or outside of the CCU 12, thereby achieving the respective functions of the RGB signal processing unit, the IR signal processing unit, and the output unit.

The RGB signal processing unit converts electrical signals of the B component, the R component, and the G component, which are output from the image sensor, into video signals displayable on the display device 13, and output the video signals to the output unit. Moreover, the IR signal processing unit converts an electrical signal of the IR component, which is output from the image sensor, into a video signal, and outputs the video signal to the output unit.

The output unit outputs at least either one of the video signals of the respective RGB color components and the video signal of the IR component to the display device 13. For example, the output unit outputs the video signals on the basis of either of a simultaneous output mode and a superposition output mode.

In the simultaneous output mode, the output unit simultaneously outputs an RGB image and an IR image on different screens. By the simultaneous output mode, the RGB image and the IR image can be compared with each other on the different screens, and an affected area can be observed. In the superposition output mode, the output unit outputs a synthetic image in which the RGB image and the IR image are superposed on each other. By the superposition output mode, for example, an affected area, which has emitted light by the ICG, can be clearly observed in the RGB image.

On the basis of the video signals output from the CCU 12, the display device 13 displays an image of an object such as an affected area on a screen. In the case of the simultaneous output mode, the display device 13 divides the screen into a plurality of screens, and displays the RGB image and the IR image on the respective screens side by side. In the case of the superposition output mode, the display device 13 displays, by one screen, the synthetic image in which the RGB image and the IR image are superposed on each other.

(Functions)

Next, a description will be given of functions of the endoscope 11 and the endoscope system 100 according to this embodiment. In the case of observing a subject by using the endoscope system 100, first, the indocyanine green (ICG) that is a fluorescent substance is administered to the subject. Thus, the ICG is accumulated on a region (affected area) of a lymph node, a tumor or the like.

Next, through the transmission cable 111z, visible light and near-infrared light are introduced into the light source connector 111 from the light-emitting device 1A or 1C. Light introduced into the light source connector 111 is guided to a distal end side of the scope 110, is projected from the imaging window 110z, and thereby irradiates the affected area and a periphery of the affected area. Light reflected by the affected area or the like and fluorescence emitted from the ICG are guided to a rear end side of the scope 110 through the imaging window 110z and the optical fiber, is converged by the relay lens 113, and enters the color separation prism in the inside of the camera head 114.

In the light incident into the color separation prism, light of the IR component, which is separated by an IR separation prism, is formed as an optical image of an infrared light component by the image sensor for the IR. Light of the B component, which is separated by a blue separation prism, is formed as an optical image of a blue component by the image sensor for blue. Light of the R component, which is separated by a red separation prism, is formed as an optical image of a red component by the image sensor for red. Light of the G component, which is separated by a green separation prism, is formed as an optical image of a green component by the image sensor for green.

The electrical signal of the IR component, which is converted by the image sensor for IR, is converted into a video signal by the IR signal processing unit in the inside of the CCU 12. The respective electrical signals of the B component, the R component, and the G component, which are individually converted by the image sensors for RGB, are converted into the respective video signals by the RGB signal processing unit in the inside of the CCU 12. The video signal of the IR component and the respective video signals of the B component, the R component, and the G component are output to the display device 13 in synchronization with one another.

When the simultaneous output mode is set in the inside of the CCU 12, the RGB image and the IR image are simultaneously displayed by two screens on the display device 13. Moreover, when the superposition output mode is set in the inside of the CCU 12, the synthetic image in which the RGB image and the IR image are superposed on each other is displayed on the display device 13.

As described above, the endoscope 11 according to this embodiment includes the medical light-emitting devices 1, 1A, 1B and 1C. Therefore, the fluorescent drug is efficiently excited and emitted by using the endoscope 11, thus making is possible to clearly observe the affected area.

It is preferable that the endoscope 11 according to this embodiment further include a detector that detects the fluorescence emitted from the fluorescent drug that has absorbed the first wavelength-converted light 7. In addition to the light-emitting devices 1, 1A, 1B and 1C, the endoscope 11 integrally includes the detector that detects the fluorescence emitted from the fluorescent drug, whereby the affected area can be specified by only the endoscope. Therefore, it is not necessary to largely open the stomach and specify the affected area as heretofore, and accordingly, it becomes possible to perform examination and treatment, which give less burden to a patient. Moreover, a doctor who uses the endoscope 11 can grasp the affected area accurately, and accordingly, it becomes possible to improve treatment efficiency.

[Method for Using Light-Emitting Device]

Next, a method for using the light-emitting device according to this embodiment will be described. The method for using the light-emitting device according to this embodiment is a method for using a light-emitting device when the light-emitting device is an illuminating device for a medical system using the fluorescence imaging method or the photodynamic therapy. The method for using the light-emitting device according to this embodiment includes the steps of: administering a fluorescent drug or a photosensitive drug to a subject; and applying first wavelength-converted light to the subject with whom the fluorescent drug or the photosensitive drug comes into contact. A detailed description will be given below of the method for using the light-emitting device according to this embodiment while dividing the method into a method for using the light-emitting device using the fluorescence imaging method, and a method for using the light-emitting device using the photodynamic therapy.

(Method for Using Light-Emitting Device Using Fluorescence Imaging Method)

First, a description will be given of the method for using the light-emitting device using the fluorescence imaging method. The method for using the light-emitting device using the fluorescence imaging method, is a using method in the case of using, as an illuminating device for a medical system, the above-described light-emitting device 1, 1A, 1B or 1C described as an example of the medical light-emitting device or in the case of using the endoscope 11, and the method uses the fluorescence imaging method. The method for using the light-emitting device using the fluorescence imaging method, includes the steps of: administering a fluorescent drug to a subject; and applying the first wavelength-converted light 7 to the subject with whom the fluorescent drug is in contact.

In the method for using the light-emitting device using the fluorescence imaging method, first, the fluorescent drug is administered to the subject, and the fluorescent drug is specifically accumulated on an affected area in the subject. As the fluorescent drug to be administered to the subject, as mentioned above, a drug can be used, which absorbs excitation light in the near-infrared light region, and further radiates fluorescence in the near-infrared light region, the fluorescence having a longer wavelength than the excitation light. As the fluorescent drug, for example, at least one selected from the group consisting of indocyanine green (ICG), a phthalocyanine-based compound, a talaporfin sodium-based compound, and a dipicolylcyanine (DIPCY)-based compound can be used.

Next, the first wavelength-converted light 7 is applied to the subject with whom the fluorescent drug is in contact. As mentioned above, the first wavelength-converted light 7 is emitted from the medical light-emitting device 1, 1A, 1B or 1C or the endoscope 11, and has a light component across at least the whole of the wavelength range of 700 nm or more and 800 nm or less. The light in the near-infrared light region is difficult to be scattered by hemoglobin and water in a living body, and is easy to penetrate the living body, and accordingly, the first wavelength-converted light 7 penetrates the living body and excites the fluorescent drug. The excited fluorescent drug radiates fluorescence in the near-infrared light region, the fluorescence having a longer wavelength than the excitation light. Then, the fluorescence emitted from the fluorescent drug as described above is detected by using the detector, thus making it possible to observe and treat the affected area in the living body.

As mentioned above, the first wavelength-converted light 7 has a light component across at least the whole of the wavelength range of 700 nm or more and 800 nm or less, and accordingly, becomes able to excite the fluorescent drug with high efficiency even when the fluorescent drug varies in properties. Moreover, when the solid-state light emitting element 2 of each of the medical light-emitting devices 1, 1A, 1B and 1C radiates laser light, an intensity of the first wavelength-converted light 7 emitted from the first phosphor 4 becomes high. Therefore, it becomes possible to excite the fluorescent drug in the subject with higher efficiency, and to radiate the long-wavelength fluorescence.

(Method for Using Light-Emitting Device Using Photodynamic Therapy)

Next, a description will be given of the method for using the light-emitting device using the photodynamic therapy. The method for using the light-emitting device using the photodynamic therapy, is a using method in the case of using, as such an illuminating device for the medical system, the above-described light-emitting device 1, 1A, 1B or 1C described as an example of the medical light-emitting device or in the case of using the endoscope 11, and the method uses the photodynamic therapy. The method for using the light-emitting device, which uses the photodynamic therapy, includes the steps of: administering a photosensitive drug to a subject; and applying the first wavelength-converted light 7 to the subject with whom the photosensitive drug is in contact. Here, the photosensitive drug means a substance that absorbs light and generates heat and reactive oxygen species. Moreover, the photosensitive drug is also called a photosensitive substance, a photosensitive compound, a photosensitizer, a heat generating substance, and the like.

In the method for using the light-emitting device using the photodynamic therapy, first, the photosensitive drug is administered to the subject, and the photosensitive drug is specifically accumulated on an affected area in the subject. As the photosensitive drug to be administered to the subject, as mentioned above, a drug can be used, which absorbs excitation light in the near-infrared light region, and generates heat and reactive oxygen species. As the photosensitive drug, for example, at least one selected from the group consisting of a phthalocyanine-based compound, a talaporfin sodium-based compound, and a porfirmer sodium-based compound can be used.

Next, the first wavelength-converted light 7 is applied to the subject with whom the photosensitive drug is in contact. As mentioned above, the first wavelength-converted light 7 is emitted from the medical light-emitting device 1, 1A, 1B or 1C or the endoscope 11, and has a light component across at least the whole of the wavelength range of 700 nm or more and 800 nm or less. The light in the near-infrared light region is difficult to be scattered by hemoglobin and water in a living body, and is easy to penetrate the living body, and accordingly, the first wavelength-converted light 7 penetrates the living body and irradiates the photosensitive drug. The photosensitive drug irradiated with the first wavelength-converted light 7 generates heat and reactive oxygen species. Then, the heat and the reactive oxygen species, which are generated from the photosensitive drug as described above, kill cancer cells, thus making it possible to treat the affected area in the living body.

As mentioned above, the first wavelength-converted light 7 has a light component across at least the whole of the wavelength range of 700 nm or more and 800 nm or less, and accordingly, becomes able to generate the heat and the reactive oxygen species from the photosensitive drug with high efficiency even when the photosensitive drug varies in properties. Moreover, when the solid-state light-emitting element 2 of each of the medical light-emitting devices 1, 1A, 1B and 1C radiates laser light, an intensity of the first wavelength-converted light 7 emitted from the first phosphor 4 becomes high. Therefore, it becomes possible to generate the heat and the reactive oxygen species from the photosensitive drug with high efficiency.

In the fluorescent drug for use in the fluorescence imaging method and the photosensitive drug for use in the photodynamic therapy, an absorption spectrum of each thereof may sometimes change in the subject due to a solvatochromic effect, a change of electron withdrawing characteristics by association, a difference in type of a functional group, a substitution group or a side chain, and the like. Here, the solvatochromic effect is an effect of changing a ground state and an excited state by a change of a solvent polarity. Moreover, the association means coupling of the same type of molecules by intermolecular force. Therefore, when the light radiated by the solid-state light-emitting element such as a laser element is light with a narrow light emission spectrum half width, such a change of the absorption spectrum of the drug cannot be sometimes dealt with. Specifically, when the light radiated by the solid-state light-emitting element is light with a narrow light emission spectrum half width, conversion efficiency of the drug from light energy to light energy and conversion efficiency of the drug from light energy to heat energy may sometimes decrease.

EXAMPLES

Example 1

(Preparation of Phosphor)

An oxide phosphor was synthesized by using a preparation method using a solid phase reaction. Specifically, an oxide phosphor represented by a composition formula of $Y_3(Ga_{0.98},Cr_{0.02})_2(GaO_4)_3$ was synthesized. Note that the following compound powders were used as main raw materials at the time of synthesizing the oxide phosphor.

Yttrium oxide ($Y_2O_3$): purity 3N, made by Shin-Etsu Chemical Co., Ltd.
Gallium oxide ($Ga_2O_3$): purity 4N, made by Nippon Rare Metal, Inc.
Chromium oxide ($Cr_2O_3$): purity 3N, made by Kojundo Chemical Laboratory Co., Ltd.

First, the above-described raw materials were weighed so as to obtain a compound with a stoichiometric composition, which was $Y_3(Ga_{0.98},Cr_{0.02})_2(GaO_4)_3$. Next, the raw materials were dry-mixed with one another by using a mortar and a pestle, and a raw material to be fired was prepared.

The above-described raw material to be fired was transferred to an alumina crucible attached with a cover, and was fired for 2 hours in an atmosphere of 1600° C. by using a box-type electric furnace, and thereafter, a fired product was lightly disintegrated. Then, a phosphor of Example 1 was obtained. Note that the fact that such a sample after the firing was $Y_3(Ga_{0.98},Cr_{0.02})_2(GaO_4)_3$ was confirmed by an X-ray diffraction method.

(Evaluation of Light Emission Spectrum)

A light emission spectrum of the phosphor of Example 1 was evaluated by using a spectrophotofluorometer (FP-6500, made by JASCO Corporation).

Example 2

(Preparation of Phosphor)

An oxide phosphor was synthesized by using a preparation method using a solid phase reaction. Specifically, an oxide phosphor represented by a composition formula of $Gd_3(Ga_{0.98},Cr_{0.02})_2(GaO_4)_3$ was synthesized. Note that the following compound powders were used as main raw materials at the time of synthesizing the oxide phosphor.

Gadolinium oxide ($Gd_2O_3$): purity 3N, made by Kojundo Chemical Laboratory Co., Ltd.
Gallium oxide ($Ga_2O_3$): purity 4N, made by Nippon Rare Metal, Inc.
Chromium oxide ($Cr_2O_3$): purity 3N, made by Kojundo Chemical Laboratory Co., Ltd.

First, the above-described raw materials were weighed so as to obtain a compound with a stoichiometric composition, which was $Gd_3(Ga_{0.98},Cr_{0.02})_2(GaO_4)_3$. Next, the raw materials were dry-mixed with one another by using a mortar and a pestle, and a raw material to be fired was prepared.

The above-described raw material to be fired was transferred to an alumina crucible attached with a cover, and was fired for 2 hours in an atmosphere of 1600° C. by using a box-type electric furnace, and thereafter, a fired product was lightly disintegrated. Then, a phosphor of Example 2 was obtained. Note that the fact that such a sample after the firing was $Gd_3(Ga_{0.98},Cr_{0.02})_2(GaO_4)_3$ was confirmed by an X-ray diffraction method.

(Evaluation of Light Emission Spectrum)

Figure 8:
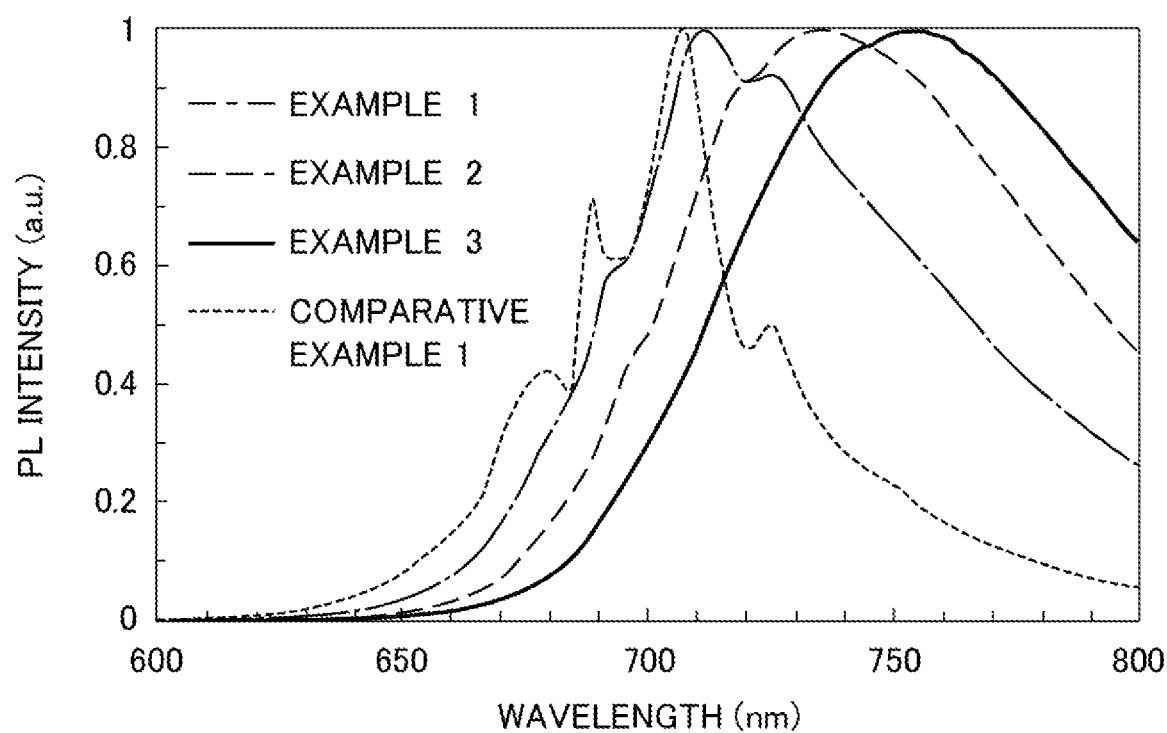
FIG. 8 is a graph illustrating relationships between wavelengths and PL intensities.

A light emission spectrum of the phosphor was evaluated in a similar way to Example 1. Results are shown in FIG. 8 and Table 1.

Example 3

(Preparation of Phosphor)

An oxide phosphor was synthesized by using a preparation method using a solid phase reaction. Specifically, an oxide phosphor represented by a composition formula of $(Gd_{0.75},La_{0.25})_3(Ga_{0.98},Cr_{0.02})_2(GaO_4)_3$ was synthesized. Note that the following compound powders were used as main raw materials at the time of synthesizing the oxide phosphor.

Gadolinium oxide ($Gd_2O_3$): purity 3N, made by Kojundo Chemical Laboratory Co., Ltd.
Lanthanum oxide ($La_2O_3$): purity 3N, made by Kojundo Chemical Laboratory Co., Ltd.
Gallium oxide ($Ga_2O_3$): purity 4N, made by Nippon Rare Metal, Inc.
Chromium oxide ($Cr_2O_3$): purity 3N, made by Kojundo Chemical Laboratory Co., Ltd.

First, the above-described raw materials were weighed so as to obtain a compound with a stoichiometric composition, which was $(Gd_{0.75},La_{0.25})_3(Ga_{0.98},Cr_{0.02})_2(GaO_4)_3$. Next, the raw materials were dry-mixed with one another by using a mortar and a pestle, and a raw material to be fired was prepared.

The above-described raw material to be fired was transferred to an alumina crucible attached with a cover, and was fired for 2 hours in an atmosphere of 1400° C. by using a box-type electric furnace, and thereafter, a fired product was lightly disintegrated. Then, a phosphor of Example 3 was obtained. Note that the fact that such a sample after the firing was $(Gd_{0.75},La_{0.25})_3(Ga_{0.98},Cr_{0.02})_2(GaO_4)_3$ was confirmed by an X-ray diffraction method.

(Evaluation of Light Emission Spectrum)

A light emission spectrum of the phosphor was evaluated in a similar way to Example 1. Results are shown in FIG. 8 and Table 1.

Comparative Example 1

(Preparation of Phosphor)

An oxide phosphor was synthesized by using a preparation method using a solid phase reaction. Specifically, an oxide phosphor represented by a composition formula of $Y_3(Al_{0.98},Cr_{0.02})_2(AlO_4)_3$ was synthesized. Note that the following compound powders were used as main raw materials at the time of synthesizing the oxide phosphor.

Yttrium oxide ($Y_2O_3$): purity 3N, made by Shin-Etsu Chemical Co., Ltd.
Aluminum oxide ($Al_2O_3$): purity 3N, made by Sumitomo Chemical Co., Ltd.
Chromium oxide ($Cr_2O_3$): purity 3N, made by Kojundo Chemical Laboratory Co., Ltd.

First, the above-described raw materials were weighed so as to obtain a compound with a stoichiometric composition, which was $Y_3(Al_{0.98},Cr_{0.02})_2(AlO_4)_3$. Next, the raw materials were dry-mixed with one another by using a mortar and a pestle, and a raw material to be fired was prepared.

The above-described raw material to be fired was transferred to an alumina crucible attached with a cover, and was fired for 2 hours in an atmosphere of 1600° C. by using a box-type electric furnace, and thereafter, a fired product was lightly disintegrated. Then, a phosphor of Comparative example 1 was obtained. Note that the fact that such a sample after the firing was $Y_3(Al_{0.98},Cr_{0.02})_2(AlO_4)_3$ was confirmed by an X-ray diffraction method.

(Evaluation of Light Emission Spectrum)

A light emission spectrum of the phosphor was evaluated in a similar way to Example 1. Results are shown in FIG. 8 and Table 1.

FIG. 8 shows a light emission spectrum when the phosphor was excited at an excitation wavelength: 450 nm. Note that FIG. 8 also shows the light emission spectra of Example 2, Example 3 and Comparative example 1.

Table 1 shows a light emission peak wavelength $\lambda_{MAX}$ that is a peak wavelength of a maximum fluorescence intensity value peak, which indicates the maximum fluorescence intensity value in the light emission spectrum. Moreover, Table 1 shows a spectrum width (80% spectrum width) $W_{80\%}$ at an 80% intensity of the light emission peak intensity of the maximum fluorescence intensity value peak. Furthermore, Table 1 shows a 780 nm fluorescence intensity ratio $L_{780\ nm}$ that is a ratio of a light emission intensity at a wavelength of 780 nm with respect to the light emission peak intensity (maximum fluorescence intensity value) at the maximum fluorescence intensity value peak of the light emission spectrum.

TABLE 1

|  | Example 1 | Example 2 | Example 3 | Comparative Example 1 |
| --- | --- | --- | --- | --- |
| $\lambda_{MAX}$ (nm) | 712 | 735 | 755 | 708 |
| $W_{80\%}$ (nm) | 33 | 54 | 62 | 11 |
| $L_{780nm}$ (%) | 39 | 65 | 84 | 9 |

(Summary of Evaluations of Light Emission Spectra)

It is found that each of the phosphors in Examples 1 to 3 radiates wavelength-converted light in which a broad spectral component having a maximum fluorescence intensity value in a wavelength region exceeding 710 nm is larger in amount than a linear spectral component having a maximum fluorescence intensity value in a wavelength region of 680 to 710 nm.

Note that the above-described linear spectral component is a light component with a long afterglow, which is based on the electron energy transition (spin-forbidden transition) of $^2T_1$ and $^2E \rightarrow ^4A_2(t_2^3)$ in $Cr^{3+}$. Moreover, the above-described broad spectral component is a light component with a short afterglow, which is based on the electron energy transition (spin-allowed transition) of $^4T_2 \rightarrow ^4A_2$.

Therefore, it is found that, in accordance with the light-emitting device using each of the phosphors in Examples 1 to 3 as the first phosphor, a point light source including a large amount of the near-infrared component can be fabricated with ease.

Moreover, it is found that, in accordance with the light-emitting device using each of the phosphors in Examples 1 to 3 as the first phosphor, a fluorescent drug or a photosensitive drug can be used without being affected by variations of wavelength dependency of sensitivity of the above-described drug in the fluorescence imaging method and the photodynamic therapy (PDT). That is, it is found that, even if the wavelength dependency of the sensitivity has variations in the fluorescent drug or the photosensitive drug, it becomes possible to cause the above-described drug to sufficiently function without being affected by the variations.

Furthermore, it is found that, in the light-emitting device using each of the phosphors in Examples 1 to 3 as the first phosphor, the first wavelength-converted light 7 includes a large amount of the fluorescent component in the near-infrared wavelength region (650 to 1000 nm) in which light easily penetrates a living body, the near-infrared wavelength region being called "biological window." Therefore, it is found that, in accordance with the light-emitting device using each of the phosphors in Examples 1 to 3 as the first phosphor, the intensity of the near-infrared light that penetrates a living body increases.

Comparative Example 2

(Preparation of Phosphor)

A nitride phosphor was synthesized by using a preparation method using a solid phase reaction. Specifically, a nitride phosphor represented by a composition formula of $(Ca_{0.997}, Eu_{0.003})AlSiN_3$ was synthesized. Note that the following compound powders were used as main raw materials at the time of synthesizing the nitride phosphor.

Calcium nitride ($Ca_3N_2$): purity 2N, made by Taiheiyo Cement Corporation

Aluminum nitride (AlN): purity 3N, made by Kojundo Chemical Laboratory Co., Ltd.

Silicon nitride ($Si_3N_4$): purity 3N, made by Denka Company Limited Europium nitride (EuN): purity 2N, made by Taiheiyo Cement Corporation First, in a glove box with an $N_2$ atmosphere, the above-described raw materials were weighed so as to obtain a compound with a stoichiometric composition, which was $(Ca_{0.997}, Eu_{0.003})AlSiN_3$. Next, the raw materials were dry-mixed with one another by using a mortar and a pestle, and a raw material to be fired was prepared.

The above-described raw material to be fired was transferred to a crucible which was made of boron nitride (BN) and attached with a cover, and was fired for 2 hours in an $N_2$-pressurized atmosphere (with 0.6 MPa) of 1600° C. by using an electric furnace with a controlled pressurized atmosphere, and thereafter, a fired product was lightly disintegrated. Then a phosphor of Comparative example 2 was obtained. Note that the fact that a sample after the firing was $(Ca_{0.997}, Eu_{0.003})AlSiN_3$ by an X-ray diffraction method.

(Evaluation of Light Emission Lifetime)

A light emission lifetime of each of the phosphors was evaluated by using a Quantaurus-Tau compact fluorescence lifetime measuring apparatus (made by Hamamatsu Photonics K.K.). Results are shown in FIG. 9 and Table 2.

Figure 9:
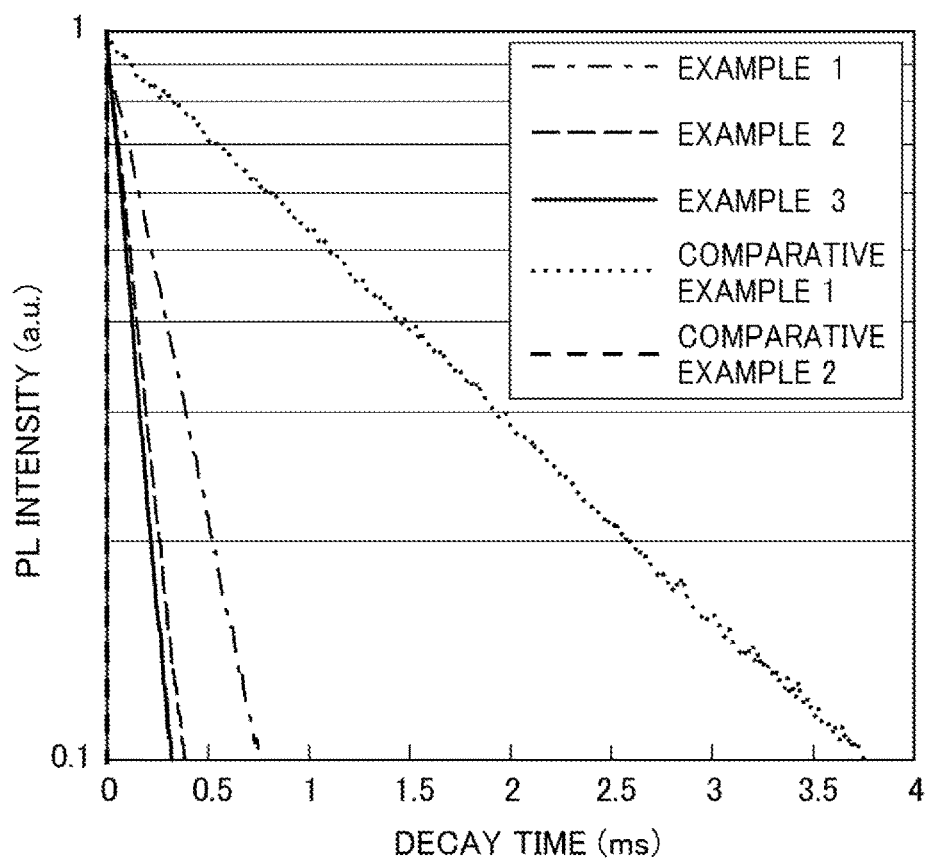
FIG. 9 is a graph illustrating relationships between decay rates and the PL intensities.

FIG. 9 shows a light emission lifetime in Example 1. Note that FIG. 9 also shows light emission lifetimes of Example 2, Example 3, Comparative example 1 and Comparative example 2.

Table 2 shows a time (1/10 afterglow): $\tau_{1/10}$ until the intensity reaches 1/10 of the maximum light emission intensity.

TABLE 2

|  | Example 1 | Example 2 | Example 3 | Comparative Example 1 | Comparative Example 2 |
| --- | --- | --- | --- | --- | --- |
| $T_{1/10}$ (ms) | 0.78 | 0.38 | 0.32 | 3.81 | 0.0017 |

(Summary of Evaluations of Light Emission Lifetime)

It is found that each of the phosphors in Examples 1 to 3 radiates wavelength-converted light in which a short-afterglow near-infrared component present in the region of the wavelength exceeding 710 nm is larger in amount than a long-afterglow linear spectral component having a maximum fluorescence intensity value in a wavelength region of 680 to 710 nm.

Note that the above-described long-afterglow linear spectral component is a light component based on electron energy transition (spin-forbidden transition) of $^2T_1$ and $^2E \rightarrow {}^4A_2$ in $Cr^{3+}$. Moreover, the above-described short-afterglow near-infrared component is a light component based on the electron energy transition (spin-allowed transition) of $^4T_2 \rightarrow {}^4A_2$.

Therefore, it is found that, in accordance with the light-emitting device using each of the phosphors in Examples 1 to 3 as the first phosphor, a large amount of the near-infrared component is included, the fluorescence output saturation when the high-light density laser light is applied is small, and it is easy to increase the output.

Example 4

(Fabrication of Sintered Body)

The mass of 1.0 g of the phosphor powder of Example 1 was molded by applying a pressure of 210 MPa thereto by a hydraulic press machine, and a powder compact with a diameter of 13 mm was fabricated. This powder compact was fired for 1 hour in an atmosphere of 1400° C. by using a box-type electric furnace, whereby a sintered body of Example 4 was obtained.

Example 5

(Fabrication of Sintered Body)

The mass of 1.0 g of the phosphor powder of Example 2 was molded by applying a pressure of 210 MPa thereto by a hydraulic press machine, and a powder compact with a diameter of 13 mm was fabricated. This powder compact was fired for 1 hour in an atmosphere of 1400° C. by using a box-type electric furnace, whereby a sintered body of Example 5 was obtained.

Example 6

(Fabrication of Sintered Body)

The mass of 1.0 g of the phosphor powder of Example 3 was molded by applying a pressure of 210 MPa thereto by a hydraulic press machine, and a powder compact with a diameter of 13 mm was fabricated. This powder compact was fired for 1 hour in an atmosphere of 1400° C. by using a box-type electric furnace, whereby a sintered body of Example 6 was obtained.

Comparative Example 3

(Fabrication of sintered body)

The mass of 0.5 g of the phosphor powder of Comparative example 2 was molded by applying a pressure of 210 MPa thereto by a hydraulic press machine, and a powder compact with a diameter of 13 mm was fabricated. This powder compact was fired for 2 hours in an $N_2$-pressurized atmosphere (with 0.6 MPa) of 1700° C. by using an electric furnace with a controlled pressurized atmosphere, whereby a sintered body of Comparative example 3 was obtained.

(Evaluation of Fluorescence Output Saturation)

With regard to fluorescence output saturation properties of the phosphor, blue LD light with a peak wavelength of 450 nm was applied to each of the phosphors by using an integrating sphere, and light emission of phosphor pellets was observed by a multi-channel spectroscope. At this time, a rated output of the blue LD light was changed from 0.93 W to 3.87 W. An irradiated area of the phosphor was set to 0.785 mm$^2$.

Figure 10:
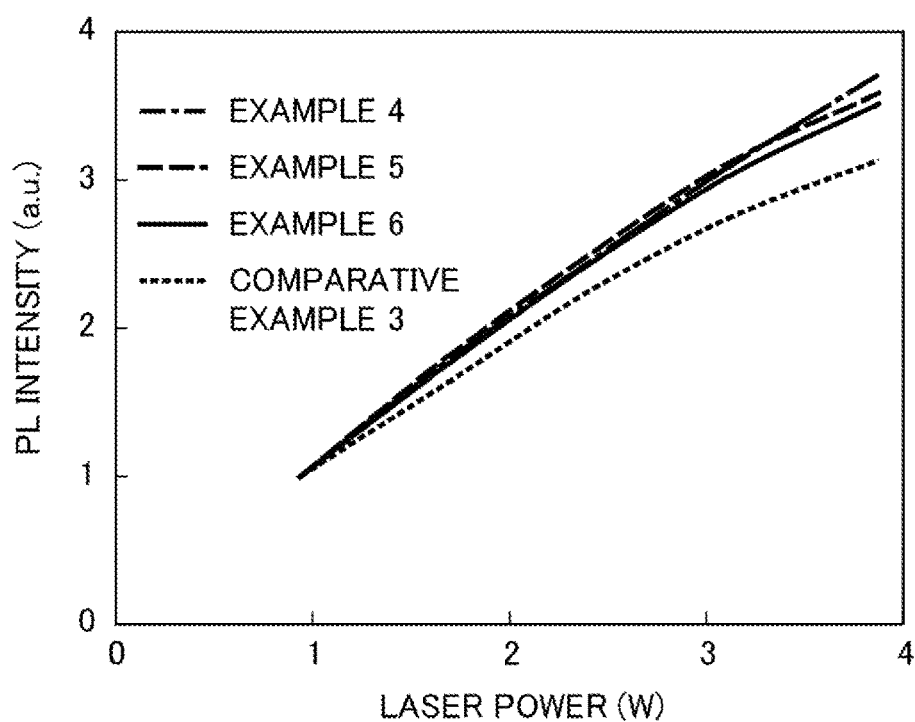
FIG. 10 is a graph illustrating relationships between excitation light power densities and the PL intensities.

FIG. 10 shows fluorescence output saturation properties of Examples 4 to 6 and Comparative example 3. It is found that the light emission lifetime of the $Cr^{3+}$-activated phosphor is extremely long as compared with the light emission lifetime of the $Eu^{2+}$-activated phosphor. Moreover, it is found that, though having a long light emission lifetime, the $Cr^{3+}$-activated phosphor maintains high light emission efficiency also in the region where the power density of the excitation light is high.

The entire contents of Japanese Patent Application No. 2018-245494 (filed on: Dec. 27, 2018) are incorporated herein by reference.

Although the contents of this embodiment have been described above in accordance with the examples, it is obvious to those skilled in the art that this embodiment is not limited to the description of these and that various modifications and improvements are possible.

INDUSTRIAL APPLICABILITY

In accordance with the present disclosure, there can be provided the light-emitting device that radiates the high-output light with a high ratio of the near-infrared fluorescent component under the excitation of the high-density laser light, the electronic device using the light-emitting device, and the method for using the light-emitting device.

REFERENCE SIGNS LIST 1, 1A, 1B, 1C Medical light-emitting device (light-emitting device)
2 Solid-state light-emitting element (light source)
3, 3A Wavelength converter
4 First phosphor
6 Primary light
7 First wavelength-converted light
8 Second phosphor
9 Second wavelength-converted light
11 Endoscope
100 Endoscope system

The invention claimed is:

1. A light-emitting device comprising:
a light source that radiates a primary light; and
a first phosphor that absorbs the primary light and converts the primary light into a first wavelength-converted light having a longer wavelength than the primary light, wherein:
the primary light is a laser light,
the first wavelength-converted light includes fluorescence based on electron energy transition of $Cr^{3+}$, the fluorescence having an afterglow of more than 10 µs based on a parity-forbidden transition,
a fluorescence spectrum of the first wavelength-converted light has a maximum fluorescence intensity value in region of a wavelength exceeding 710 nm, and
the light source is a solid-state light-emitting element with a rated light output of 1 W or more, wherein saturation of the fluorescence based on the parity-forbidden transition of $Cr^{3+}$ is less likely to occur under excitation by the primary light relative to saturation of fluorescence based on a parity-allowed transition of $Ce^{3+}$ or $Eu^{2+}$ having an afterglow of 10 µs or less.

2. The light-emitting device according to claim 1, wherein the fluorescence spectrum of the first wavelength-converted light does not include a trail of a linear spectral component, the trail being derived from the electron energy transition of $Cr^{3+}$.

3. The light-emitting device according to claim 1, wherein the first phosphor does not include an activator other than $Cr^{3+}$.

4. The light-emitting device according to claim 1, wherein the first phosphor has a crystal structure of garnet.

5. The light-emitting device according to claim 1, further comprising a second phosphor that absorbs the primary light and converts the primary light into second wavelength-converted light that has a longer wavelength than the primary light and is different from the first wavelength-converted light.

6. The light-emitting device according to claim 1, wherein the first phosphor includes two or more types of a $Cr^{3+}$-activated phosphor.

7. The light-emitting device according to claim 1, wherein a light density of the primary light exceeds 0.5 W/mm².

8. The light-emitting device according to claim 1, wherein the primary light is at least either one of cold color light having a maximum fluorescence intensity value within a wavelength range of 400 nm or more and less than 500 nm and warm color light having a maximum fluorescence intensity value within a wavelength region of 570 nm or more and less than 660 nm.

9. The light-emitting device according to claim 1, wherein the light-emitting device is a medical light source or a medical illuminating device.

10. The light-emitting device according to claim 9, wherein the light-emitting device is an illuminating device for a medical system using a fluorescence imaging method or a photodynamic therapy.

11. The light-emitting device according to claim 1, wherein the light-emitting device is a light source for a sensing system or an illuminating system for a sensing system.

12. The light-emitting device according to claim 1, wherein the light-emitting device is a medical light-emitting device.

13. An electronic device comprising:
the light-emitting device according to claim 9.

14. A method for using the light-emitting device according to claim 10, wherein
the light-emitting device is an illuminating device for a medical system using a fluorescence imaging method or a photodynamic therapy, and
the method comprises:
a step of administering a fluorescent drug or a photosensitive drug to a subject; and
applying the first wavelength-converted light to the subject with whom the fluorescent drug or the photosensitive drug is in contact.

15. A light-emitting device comprising:
a light source that radiates a primary light; and
a first phosphor that absorbs the primary light and converts the primary light into a first wavelength-converted light having a longer wavelength than the primary light, wherein:
the primary light is a laser light,
the first wavelength-converted light includes fluorescence based on electron energy transition of $Cr^{3+}$, the fluorescence having an afterglow of more than 10 μs based on a parity-forbidden transition,
an 80% spectrum width in a maximum fluorescence intensity value peak of the first wavelength-converted light is 20 nm or more and less than 80 nm, and
the light source is a solid-state light-emitting element with a rated light output of 1 W or more, wherein saturation of the fluorescence based on the parity-forbidden transition of $Cr^{3+}$ is less likely to occur under excitation by the primary light relative to saturation of fluorescence based on a parity-allowed transition of $Ce^{3+}$ or $Eu^{2+}$ having an afterglow of 10 μs or less.

16. A light-emitting device comprising:
a light source that radiates primary light; and
a first phosphor that absorbs the primary light and converts the primary light into first wavelength-converted light having a longer wavelength than the primary light, wherein:
the primary light is laser light,
the first wavelength-converted light includes fluorescence based on electron energy transition of $Cr^{3+}$, the fluorescence having an afterglow of more than 10 μs based on a parity-forbidden transition,
a ratio of a fluorescence intensity of a fluorescence spectrum of the first wavelength-converted light at a wavelength of 780 nm with respect to a maximum fluorescence intensity value of the first wavelength-converted light exceeds 30%, and the light source is a solid-state light-emitting element with a rated light output of 1 W or more, wherein saturation of the fluorescence based on the parity-forbidden transition of $Cr^{3+}$ is less likely to occur under excitation by the primary light relative to saturation of fluorescence based on a parity-allowed transition of $Ce^{3+}$ or $Eu^{2+}$ having an afterglow of 10 μs or less.

17. A light-emitting device comprising:
a light source that radiates primary light; and
a first phosphor that absorbs the primary light and converts the primary light into first wavelength-converted light having a longer wavelength than the primary light, wherein:
the primary light is laser light,
the first wavelength-converted light includes fluorescence based on electron energy transition of $Cr^{3+}$, the fluorescence having an afterglow of more than 10 μs based on a parity-forbidden transition, and
a 1/10 afterglow of the first wavelength-converted light is less than 1 ms, and the light source is a solid-state light-emitting element with a rated light output of 1 W or more, wherein saturation of the fluorescence based on the parity-forbidden transition of $Cr^{3+}$ is less likely to occur under excitation by the primary light relative to saturation of fluorescence based on a parity-allowed transition of $Ce^{3+}$ or $Eu^{2+}$ having an afterglow of 10 μs or less.

* * * * *